United States Patent
Brush et al.

(10) Patent No.: US 11,488,695 B2
(45) Date of Patent: Nov. 1, 2022

(54) EXPRESSION OF CLINICAL LOGIC WITH POSITIVE AND NEGATIVE EXPLAINABILITY

(71) Applicant: CERNER INNOVATION, INC., Kansas City, KS (US)

(72) Inventors: Ryan Alan Brush, Overland Park, KS (US); Paul Hartwell, Olathe, KS (US); Mike Rodriguez, Overland Park, KS (US)

(73) Assignee: CERNER INNOVATION, INC., North Kansas City, MO (US)

( * ) Notice: Subject to any disclaimer, the term of this patent is extended or adjusted under 35 U.S.C. 154(b) by 0 days.

(21) Appl. No.: 16/727,405

(22) Filed: Dec. 26, 2019

(65) Prior Publication Data

US 2020/0135308 A1   Apr. 30, 2020

Related U.S. Application Data

(63) Continuation of application No. 14/258,350, filed on Apr. 22, 2014, now Pat. No. 10,566,080, which is a continuation-in-part of application No. 14/046,699, filed on Oct. 4, 2013, now Pat. No. 11,238,988, which is a continuation-in-part of application No. 13/803,459, filed on Mar. 14, 2013, now abandoned.

(51) Int. Cl.
*G16H 10/60*   (2018.01)
*G16H 50/20*   (2018.01)
*G06Q 40/08*   (2012.01)

(52) U.S. Cl.
CPC .............. *G16H 10/60* (2018.01); *G06Q 40/08* (2013.01); *G16H 50/20* (2018.01)

(58) Field of Classification Search
CPC ...................................................... G16H 10/60
See application file for complete search history.

(56) References Cited

U.S. PATENT DOCUMENTS

| | | |
|---|---|---|
| 6,915,265 B1 | 7/2005 | Johnson |
| 2004/0103001 A1 | 5/2004 | Mazar et al. |
| 2005/0182665 A1 | 8/2005 | Abraham-Fuchs et al. |
| 2007/0174252 A1 | 7/2007 | Rawlings et al. |
| 2011/0301982 A1 | 12/2011 | Green, Jr. et al. |
| 2012/0166426 A1 | 6/2012 | Milward et al. |
| 2012/0215560 A1* | 8/2012 | Ofek .................. G06Q 10/10 705/3 |
| 2013/0144790 A1 | 6/2013 | Clements |
| 2013/0226870 A1 | 8/2013 | Dash |
| 2014/0256047 A1 | 9/2014 | Lee et al. |
| 2014/0257047 A1* | 9/2014 | Sillay .................. H04L 63/10 600/595 |

(Continued)

*Primary Examiner* — Robert A Sorey
*Assistant Examiner* — Kristine K Rapillo
(74) *Attorney, Agent, or Firm* — Shook, Hardy & Bacon L.L.P.

(57) ABSTRACT

Methods, systems, and computer-storage media are provided for facilitating the management of population health. A parallel processing architecture receives patient population health data from healthcare facilities along with any updated data. A high-level clinical logic is executed against the data to identify, among other things, patients in the population who qualify for health intervention programs. Using this information, healthcare facilities can implement management programs to help care for these patients.

20 Claims, 12 Drawing Sheets

(56) References Cited

U.S. PATENT DOCUMENTS

2014/0278481 A1 9/2014 Brush
2014/0278519 A1 9/2014 Brush et al.
2014/0278527 A1 9/2014 Brush

* cited by examiner

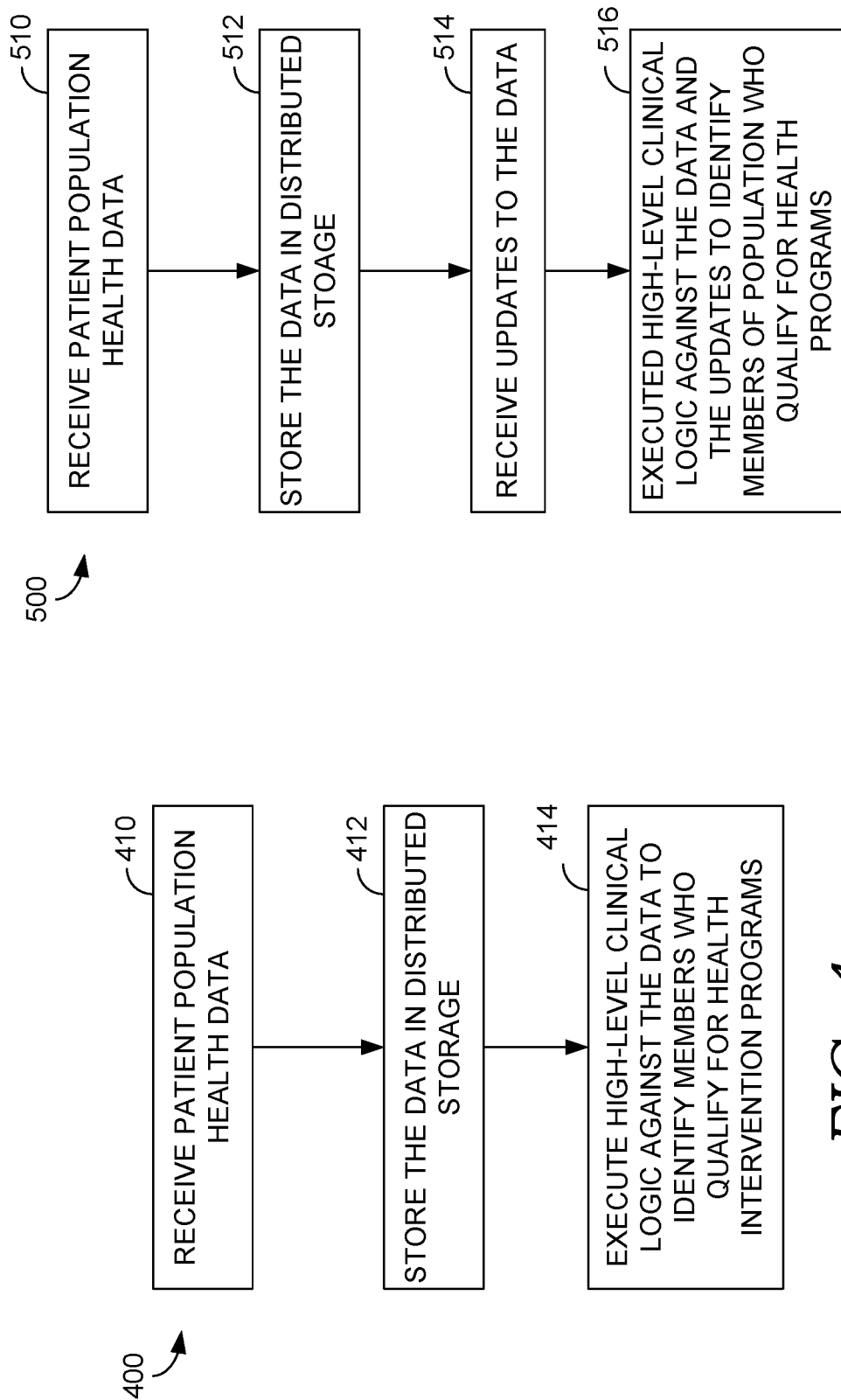

EXPRESSION OF CLINICAL LOGIC WITH POSITIVE AND NEGATIVE EXPLAINABILITY

CROSS REFERENCE TO RELATED APPLICATIONS

This application, is a Continuation of U.S. patent application Ser. No. 14/258,350, filed Apr. 22, 2014, entitled "Expression of Clinical Logic with Positive and Negative Explainability," which is a Continuation-In-Part application of U.S. patent application Ser. No. 14/046,699, filed Oct. 4, 2013, entitled "Large Scale Identification and Analysis of Population Health Risks;" which is a Continuation-in-Part application of U.S. patent application Ser. No. 13/803,459, filed Mar. 14, 2013, entitled "Large Scale Identification and Analysis of Population Health Risks." Both of these applications are incorporated by reference in their entirety.

BACKGROUND

Healthcare facilities are taking on increasing responsibility for managing the overall health of population segments serviced by the facilities. This is partly in response to insurance payment models that provide for additional payments to the healthcare facilities when certain segments within the population meet qualifying criteria. For example, additional payments may be made to the healthcare facilities when patients within an identified diabetic population segment have blood glucose values and other lab results within a predefined range.

Traditional systems are ill-adapted to meet the requirements of population health management. For example, traditional systems are often unnecessarily complex and inflexible. They are unable to meet emerging needs or to scale to meet the demands associated with processing the large volumes of health data associated with the population segments. For example, a population segment associated with a healthcare facility may encompass up to 2,000,000 or more patients. Very few healthcare facilities have the processing power to effectively manage population segments this large. As well, current processing logic used in population health management is often tied to specific data formats or structures, and lacks the extensibility to be executed against data in varying formats.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief, and at a high level, the present invention is directed to methods, systems, and computer-storage media for enabling a healthcare facility to manage the health of population segments. Management may include identifying members of a population who qualify for health intervention programs, stratifying identified members based on degree of risk, and monitoring ongoing health data for the identified members to determine the effectiveness of the program. Patient population health data is received and stored in association with a distributed storage system. One or more documents in human-readable form are also received and are translated into computer-readable code by defining concepts and concept-specific functions within the document based on data in the document. Parallel processors coupled to the storage system execute simple, descriptive clinical logic against the population data to identify members who qualify for the health intervention programs. Clinical logic is further utilized to stratify the members based on degree of risk and to monitor the ongoing health of the members.

BRIEF DESCRIPTION OF THE DRAWINGS

Embodiments are described in detail below with reference to the attached drawing figures, wherein:

FIG. 4 is a flow diagram of an exemplary method of utilizing patient population health data to identify members of a population who qualify for one or more health intervention programs in accordance with an embodiment of the present invention;

FIG. 5 is a flow diagram of an exemplary method of utilizing population health data including any updates to the data to identify members of a population who qualify for one or more health intervention programs in accordance with an embodiment of the present invention;

DETAILED DESCRIPTION

Figure 1:
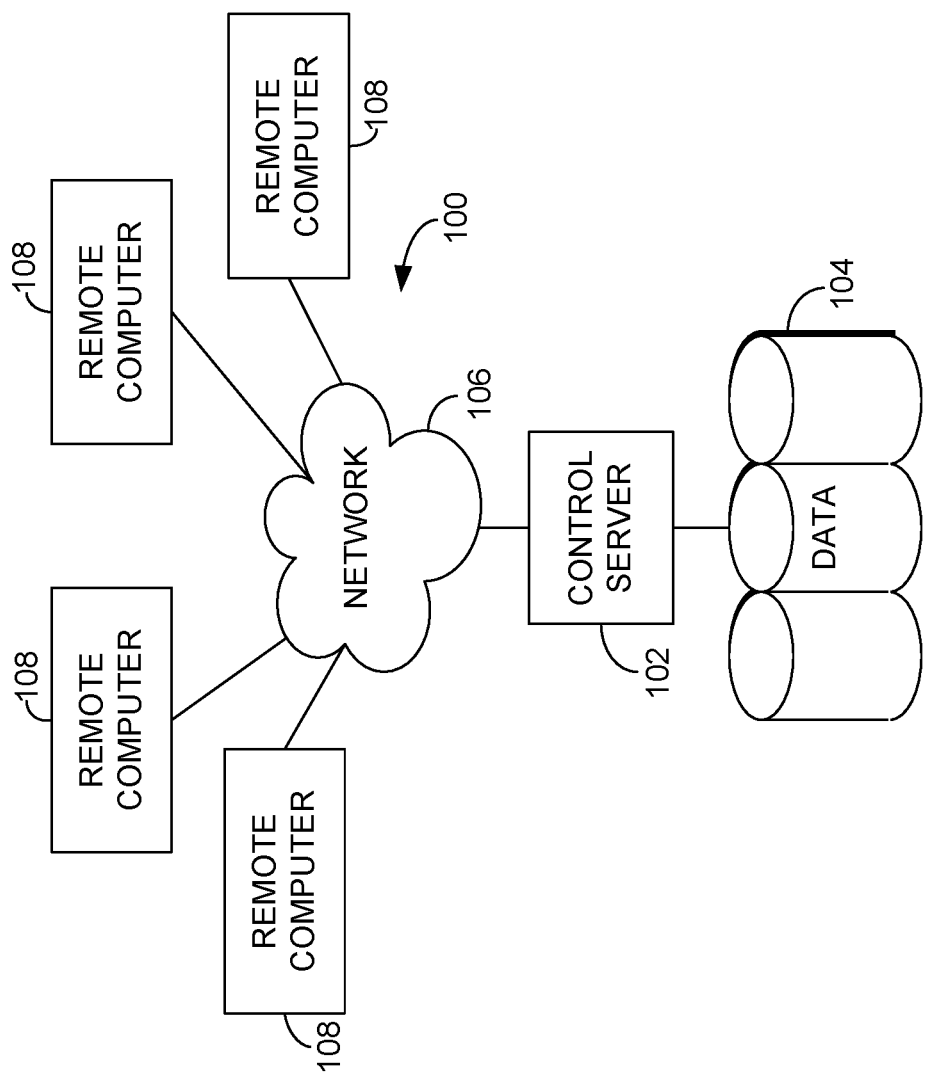
FIG. 1 is a block diagram of an exemplary computing environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

The present invention is directed to methods, systems, and computer-storage media for enabling a healthcare facility to manage the health of population segments. Management may include identifying members of a population who qualify for health intervention programs, stratifying identified members based on degree of risk, providing condition-specific recommendations, and monitoring ongoing health data for the identified members to determine the effectiveness of intervention strategies. Patient population health data is received and stored in association with a distributed storage system. Parallel processors coupled to the storage system execute simple, descriptive clinical logic against the population data to identify members who qualify for the health intervention programs. The same logic is used to process any updated data as it enters the system. Clinical logic is further utilized to stratify the members based on degree of risk, determine condition-specific recommendations, monitor the ongoing health of the members, and the like.

In a first aspect, one or more computer-storage media having computer-executable instructions embodied thereon are provided that, when executed by a computing device, facilitate a method of identifying members of a population who qualify for a health intervention program. The method includes receiving one or more sets of patient population health data, receiving a document in human-readable form, the document corresponding to the health intervention program, and generating computer-readable code that corresponds to the document in human-readable form, the computer-readable code comprising high-level clinical logic Further, the method includes storing the computer-readable code that corresponds to the document in human-readable form in association with a distributed storage system and executing the set of high-level clinical logic against the one or more sets of patient population health data to identify one or more members of the population who qualify for the health intervention program.

In a second aspect, a computer-implemented system is provided for processing population health data. The system includes a runtime engine that comprises a receiving component. The receiving component is operable to receive one or more sets of patient population health data, and receive a document in human-readable form, the document corresponding to the health intervention program. The runtime engine further includes a conversion component operable to identify, from the document, one or more concepts and one or more concept-specific functions associated with the one or more concepts, define the one or more concepts and the one or more concept-specific functions based on data in the document, and generate computer-readable code that corresponds to the document utilizing the defined one or more concepts and the one or more concept-specific functions, the computer-readable code comprising a set of high-level clinical logic. Further, the runtime engine includes a plurality of batch processing nodes operable to execute the set of high-level clinical logic against the one or more sets of patient population health data to identify one or more members of the population who qualify for the health intervention programs.

In a third aspect, one or more computer-storage media having computer-executable instructions embodied thereon are provided that, when executed by a computing device, facilitate of method of identifying members of a population who qualify for a health intervention program. The method includes receiving one or more sets of patient population health data, receiving a document in human-readable form, and from the document, identifying one or more concepts and one or more concept-specific functions associated with the one or more concepts. The method further includes defining the one or more concepts and the one or more concept-specific functions based on data in the document and generating computer-readable code that corresponds to the document utilizing the defined one or more concepts and the one or more concept-specific functions, the computer-readable code comprising a set of high-level clinical logic. The method also includes executing the set of high-level clinical logic against the one or more sets of patient population health data to identify one or more members of the population who qualify for the health intervention program.

Having provided a high-level overview of the present invention, an exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multi-processor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise non-transitory computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and providers' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information may also be entered via use of gestures such as tapping, swiping, dragging, pinching, and the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
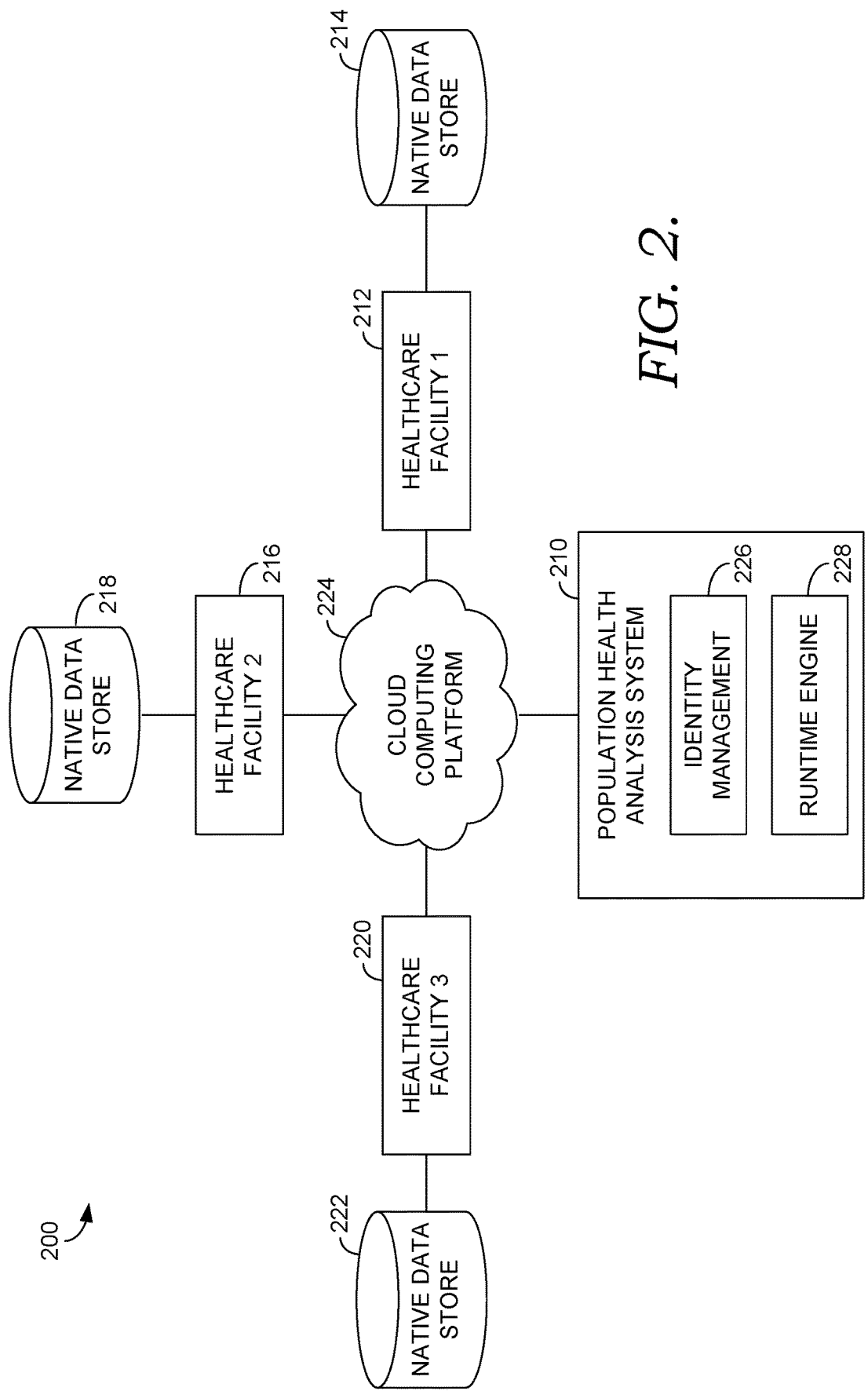
FIG. 2 is a block diagram showing an exemplary architecture for facilitating the aggregation and processing of patient population health data suitable to implement embodiments of the present invention.

Turning now to FIG. 2, a block diagram 200 is illustrated, in accordance with an embodiment of the present invention, showing an exemplary cloud computing platform 224 for use by a population health analysis system 210. It will be understood and appreciated that the cloud computing platform 224 shown in FIG. 2 is merely an example of one suitable computing system environment and is not intended to suggest any limitation as to the scope of use or functionality of embodiments of the present invention. For instance, the cloud computing platform 224 may be a public cloud, a private cloud, or a dedicated cloud. Neither should the cloud computing platform 224 be interpreted as having any dependency or requirement related to any single component or combination of components illustrated therein. Further, although the various blocks of FIG. 2 are shown with lines for the sake of clarity, in reality, delineating various components is not so clear, and metaphorically, the lines would more accurately be grey and fuzzy. In addition, any number of physical machines, virtual machines, data centers, endpoints, or combinations thereof may be employed to achieve the desired functionality within the scope of embodiments of the present invention. As mentioned, the cloud computing platform 224 comprises a cloud-computing network, which is known in the art as "the cloud."

The cloud computing platform 224 includes a data center configured to host and support the operation of the system 210. The system 210 refers to any software, or portions of software, that runs on top of, or accesses storage locations within, the platform 224. It will be appreciated that cloud computing platform 224 may include multiple computing devices such as computing devices or portions of computing devices 100 shown in FIG. 1. Cloud computing platform 224 may include virtual machines, such as software, applications, operating systems, or programs that are executed by a processing unit to underlie the functionality of the population health analysis system 210. Further, the virtual machines may include processing capacity, storage locations, and other assets to support the population health analysis system 210.

In one aspect, the cloud computing platform 224 can communicate internally through connections dynamically made between the virtual machines and computing devices and externally through a physical network topology to resources of a remote network such as with healthcare facilities 212, 216, and 220. By way of example, the connections may include, without limitation, one or more local area networks (LANs) and/or wide area networks (WANs). Such networking environments are commonplace in offices, enterprise-wide computer networks, intranets, and the Internet. Accordingly, the network is not further described herein.

As shown in FIG. 2, the population health analysis system 210 is capable of communicating with a number of different data sources, such as the healthcare facilities 212, 216, and 220 for the collection of patient population health data. Other exemplary data sources may include raw claims data, continuity of care documents (CCDs), and the like. As used throughout this application, the term "patient population health data" is meant to be broad and encompass many types of healthcare information found in a healthcare environment. For example, patient population health data may include information that describes various aspects of the patient state, including patient vitals, lab results, medication orders, diagnosis codes, condition codes, clinical orders, indexed values from clinical notes or other text documents, patient demographic information, patient history, patient images, and a variety of other patient information.

The healthcare facilities 212, 216, and 220 may include, for example, hospitals, physician offices, health information exchanges, nursing homes, pharmacies, home health services, urgent care clinics, and the like. The healthcare facilities 212, 216, and 220 may develop intervention programs designed to reduce the morbidity and mortality associated with certain widespread health problems such as hypertension, diabetes, smoking, and obesity. The intervention programs utilize a multi-disciplinary team consisting of health coaches, physicians, dieticians, pharmacists, etc. to care for patients who are enrolled in the program. Identification of patients who qualify for enrollment in these programs is important in ensuring the program's success.

In one aspect, the healthcare facilities 212, 216, and 220 may be part of a larger healthcare organization. As used throughout this application, a healthcare organization may comprise a single healthcare facility with an associated group of healthcare providers such as physicians, pharmacists, nurses, health coaches, therapists, and the like. A healthcare organization may also comprise a network of healthcare facilities such as the healthcare facilities 212, 216, and 220, each healthcare facility having an associated group of healthcare providers. The healthcare organization may create such networks in order to achieve certain financial and/or clinical objectives. For example, the healthcare organization may create such a network in order to manage the health of a population segment.

It should be noted that the healthcare facilities shown as communicating with the population health analysis system 210 in FIG. 2 are provided by way of example only and are not intended to limit the scope of the present invention in any way. Each healthcare facility 212, 216, and 220 may have one or more computing devices such as computing device 100 of FIG. 1, for communicating with the population health analysis system 210. Each healthcare facility 212, 216, and 220 maintains its own native electronic medical record system represented by a native data store (1) 214, a native data store (2) 218, and a native data store (3) 222 associated with the first, second, and third healthcare facilities respectively. Further, the healthcare facilities 212, 216, and 220 may not be directly or indirectly connected with one another such that the native data stores 214, 218, and 222 are utilized only by the data stores' respective healthcare facility. The healthcare facilities 212, 216, and 220 send information to the cloud computing platform 224 and not typically directly between one another. In addition, communication between the system 210 and the various healthcare facilities 212, 216, and 220 may be via one or more networks, which may comprise one or more wide area networks (WANs) and one or more local area networks (LANs), as well as one or more public networks, such as the Internet, and one or more private networks.

Further, the healthcare facilities 212, 216, and 220 may be able to access the system 210 in a variety of ways within the scope of the present invention. For example, in some embodiments, a healthcare facility may have a native clinical computing system, which may be able to communicate with the system 210. In other embodiments, a client application associated with the system 210 may reside or partially reside on one or more of the healthcare facility's computing devices facilitating communication with the system 210. In further embodiments, communication may simply be a web-based communication, using, for example, a web browser to communicate to the system 210 via the Internet. Any and all such variations are contemplated to be within the scope of embodiments of the present invention.

The population health analysis system 210 is available in the cloud computing platform 224 in a manner that enables cross-venue recognition of a patient through the use of a patient identity management component 226 such as an Electronic Master Person Index (EMPI). Patient identity management component 226 enables the system 210 to match data for the same patient that originates from different healthcare facilities or sources. Processing elements of a runtime engine 228 receive patient population health data that is sent to the cloud platform 224 by the healthcare facilities 212, 216, and 220 and use this information, among other things, to identify members of the population that qualify for one or more health intervention programs. This information may be used, in turn, by the healthcare facilities 212, 216, and 220 (or by a healthcare organization composed of the healthcare facilities 212, 216, and 220) to manage the health of population segments for which the healthcare facilities 212, 216, and 220 provide care.

Figure 3:
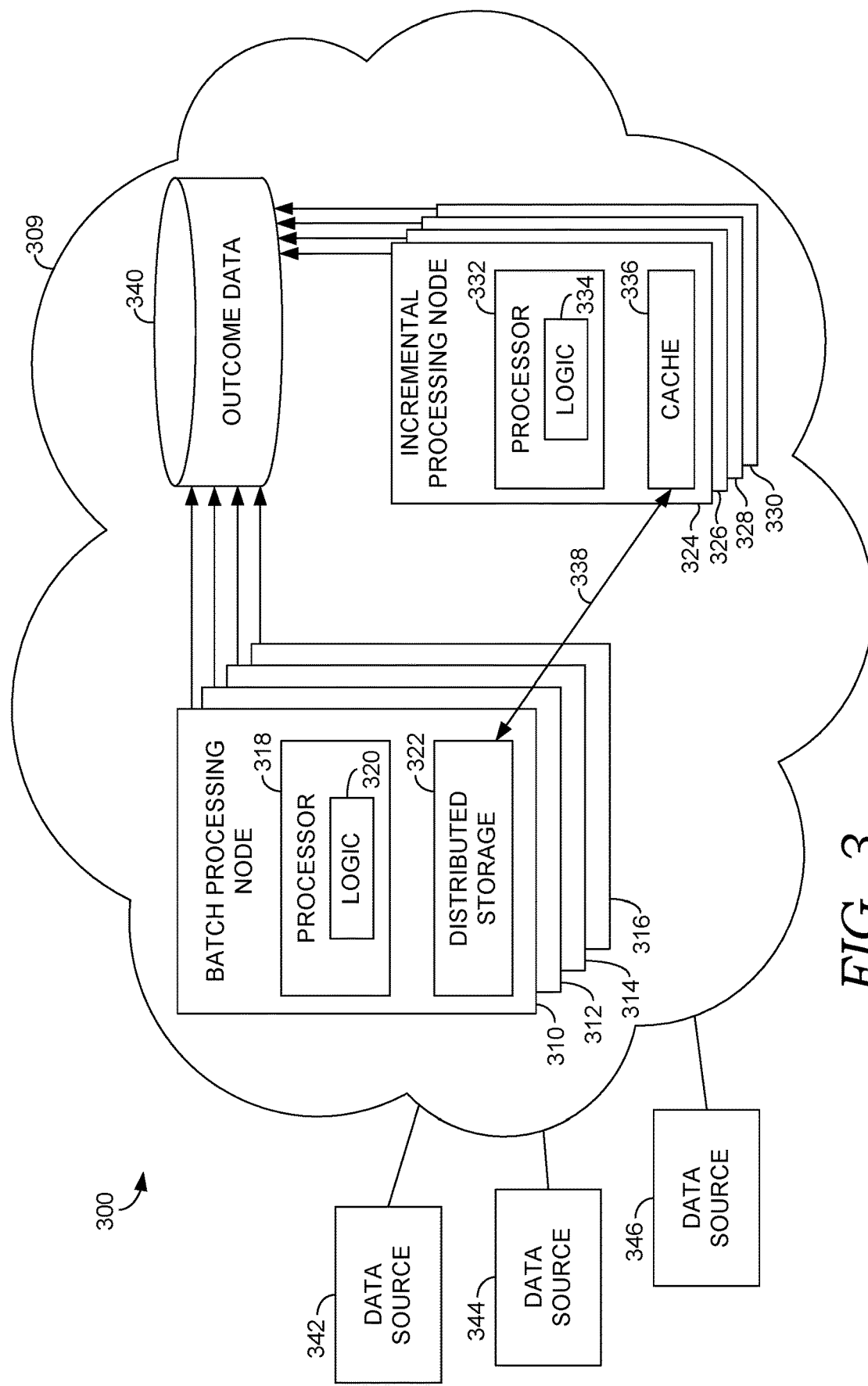
FIG. 3 is a block diagram of an exemplary system for, among other things, identifying members of a population who qualify for one or more health intervention programs suitable to implement embodiments of the present invention.

FIG. 3 depicts a more detailed view of the runtime engine 228 of FIG. 2 (now labeled as runtime engine 309 in system 300). The runtime engine 309 includes a plurality of batch processing nodes 310, 312, 314, and 316, a plurality of incremental processing nodes 324, 326, 328, and 330, and outcome data 340 stored in an outcome data store 340. Although a plurality of batch processing nodes and a plurality of incremental processing nodes are shown, the following discussion will generally reference only the batch processing node 310 and the incremental processing node 324. However, the discussion with respect to these nodes is equally applicable to the remaining batch processing nodes 312, 314, and 316, and the remaining incremental processing nodes 326, 328, and 330.

FIG. 3 includes data sources 342, 344, and 346. The data sources 342, 344, and 346 may include native data stores associated with one or more healthcare facilities such as the native data stores 214, 218, and 222 of FIG. 2. As well, the data sources 342, 344, and 346 may include raw claims data, CCD, and the like. The data sources 342, 344, and 346 store information including patient records, such as electronic medical records (EMRs) for patients that make up one or more patient population segments The patient information stored in association with the data sources 342, 344, and 346 is received by the runtime engine 309 by one of several methods. For instance, the runtime engine 309 may include, in one aspect, a program that synchronizes data from the data sources 342, 344, and 346 to the runtime engine 309 (hereinafter known as the "synchronization process"). The synchronization process extracts relevant information for a particular patient from the patient's EMR. The information may include a complete historical record of a patient's EMR. The information extracted by the synchronization process may also include any updates or modifications to the patient's EMR. Updates are received by the runtime engine 309 substantially simultaneously with when the information is updated in the patient's EMR. In another aspect, the runtime engine 309 may query the data sources 342, 344, and 346 to obtain patient information. Using these methods, for example, the runtime engine 309 receives patient population health data for a multitude of patients.

The collected patient population health data may be received in any number of structures or formats. For example, health data may be received from one data source in a relational format but be received by another data source in a hierarchical format. Further, the health data received from both of these data sources may be directed to a single piece of data such as, for example, a blood glucose level. Thus, blood glucose levels may be received in multiple different formats depending upon the characteristics of the EMR system from which they were received. Additional structures or formats include HL7 feeds, Continuity of Care Documents (CCDs), and electronic data interchange (EDI) files containing medical claims information.

The raw patient population health data may be converted into one or more standardized structures prior to being stored in a distributed storage system associated with the plurality of batch processing nodes 310, 312, 314, and 316. Additionally, the now-standardized data may be mapped or grouped into certain high-level concepts prior to being stored in the distributed storage system.

Concept mapping and/or concept grouping may be defined as converting the raw data received from the data sources 342, 344, and 346, into high-level, domain-specific constructs using a system logic. For example, a piece of raw data that describes a condition may be converted into a clinically-useful fact that a given patient has, for example, Diabetes. The system logic (e.g., system.clj) is employed to convert the raw data into one or more high-level constructs. An example of the system logic is provided below in Example 1:

```
;;; Set the concept library to be used for this program.        (Example 1)
(concept-context < CONCEPT-SYSTEM-IDENTIFIER >)
(defrule standard_diabetic_condition
(clinical-newest from Condition (and (has-concept? conditionCode "DIABETES")
                                     (has-concept? classification "DISCHARGE")))
→ (insert DiabetesCondition)
```

The "concept-context" line shows a unique identifier of the concept grouping content being used.

The batch processing node 310 of the runtime engine 309 includes a processor 318 executing a high-level clinic logic 320 and distributed storage 322. The distributed storage 322 stores the patient population health data after standardization and concept mapping/grouping. In one aspect, the distributed storage 322 maintains a complete historical electronic medical record for one or more patients associated with the batch processing node 310.

The use of storage systems associated with each of the batch processing nodes 310, 312, 314, and 316 is important in supporting the large amounts of data associated with population health (e.g., petabyte-scale data sets). As well, using distributed storage systems eliminates the need to send existing data over networks or consume external resources. The distributed storage 322 stores all clinical information relating to a patient instead of spreading the patient's information across multiple processing nodes. This facilitates accessing and processing the information at substantially the same time.

The processor 318 executes the high-level clinical logic 320 against the patient population health data stored in association with the distributed storage 322 in order to, among other things, identify members of the population that qualify for health intervention programs such as a hypertension management program or a diabetes management program. The high-level clinical logic 320 may also be used to stratify identified members based on degree of risk, provide condition-specific recommendations, and monitor the ongoing health of identified members. The logic 320 is a healthcare-domain-specific clinical logic that takes the high-level constructs generated by the system logic (e.g., Example 1 above) and generates clinically-useful results. The logic 320 has several characteristics. First, it is a declarative, descriptive language which, rather than defining actions based on traditional "if-this-then-that" logic, simply describes the set of data that is of interest using high-level concepts. For example, sample code that executes on the high-level construct DiabetesCondition generated above in Example 1 may include:

```
(defrule hba1c_less_than_7_met                                   (Example 2)
(DiabetesCondtion [identified ==true])
```

```
(LeastHba1cResult [clinical-value (this) < 7])
→ (insert Hba1cLessThan7 "ME" "Display Text"))
```

In another example, the logic 320 may be used to identify patients who qualify for a hypertension management program:

```
(defrule in_population                              (Example 3)
    "Determine if the person is in the population"
    (demographics [age > 18 and age < 76])
    (Diagnosis [type = :hypertension])
    (Encounter [type = :inpatient])
    → (insert InHypertensionPopulation))
```

As seen in Example 3, the logic 320 simply declares the conditions under which the patient is considered to be part of the hypertensive population. That fact is then inserted into the working knowledge for that patient and may be leveraged by other declarative actions. The logic 320 can also be utilized to declare new concepts. For example, a concept regarding diastolic blood pressure may be defined as follows in Example 2:

```
(defconcept DiastolicBP                             (Example 4)
    from ClinicalResult
    where type_cd in diastolic_bp_nomenclature))
```

Downstream logic can then leverage the presence of this concept rather than deal with the complexity of the underlying clinical models. For example, the statement that follows determines if the patient has high diastolic blood pressure and inserts that into the working knowledge of the patient:

```
(defrule high_diastolic_bp                          (Example 5)
(DiastolicBP [value > 90 and value < 100]) → (insert HighDiastolicBP))
```

Because the logic 320 is declarative and defers to the runtime engine 309 to provide its data, it can be executed across an arbitrary number of processors with linear scalability. This means that a set of rules can be defined once and executed in a large cluster of processing nodes without having to move data resulting in the ability to analyze very large populations significantly faster than was previously possible. For example, health data associated with approximately 2,000,000 patients can be processed by eight batch processing nodes in less than 15 minutes in order to identify and classify patients within this segment into hypertension and diabetes management programs.

Second, and as shown above, the logic 320 is structured to enable code in high-level clinical language by leveraging the use of concept mapping and/or concept grouping. As explained above, concept mapping and/or concept grouping are techniques where low-level identifiers are translated into high-level concepts with simple semantics. Thus, instead of logic that acts on numeric codes or concept identifiers, the logic 320 can act on first-class concepts. For example, traditional logic may act on code value XYZ in SNOMED, while the logic 320 can execute against a higher-level concept defined by concept grouping system logic such as, for example, "SystolicBloodPressure."

Third, the logic 320 views code as data meaning that the code in the logic 320 is actually a data structure that can be read, explored, and manipulated like other data structures. The logic 320 also provides facilities for exploring these data structures by visually rendering the data structures on a graphical user interface. The visual representations are rendered directly from the logic's data structure without any additional metadata. This feature enables interactive interfaces where a user can edit the logic 320 visually by adding, removing, and editing descriptions in each box of the visual representation. The logic 320 is also searchable to find specific pathways. This feature is important for troubleshooting problems and/or for implicitly creating audit trails. Contrast this with traditional logic where programmers must often explicitly bookmark certain pieces of data that are later used to create an audit trail. Because the logic 320 employs high-level clinical language, logic editors can include clinicians with no working knowledge of computer programming.

Figure 6:
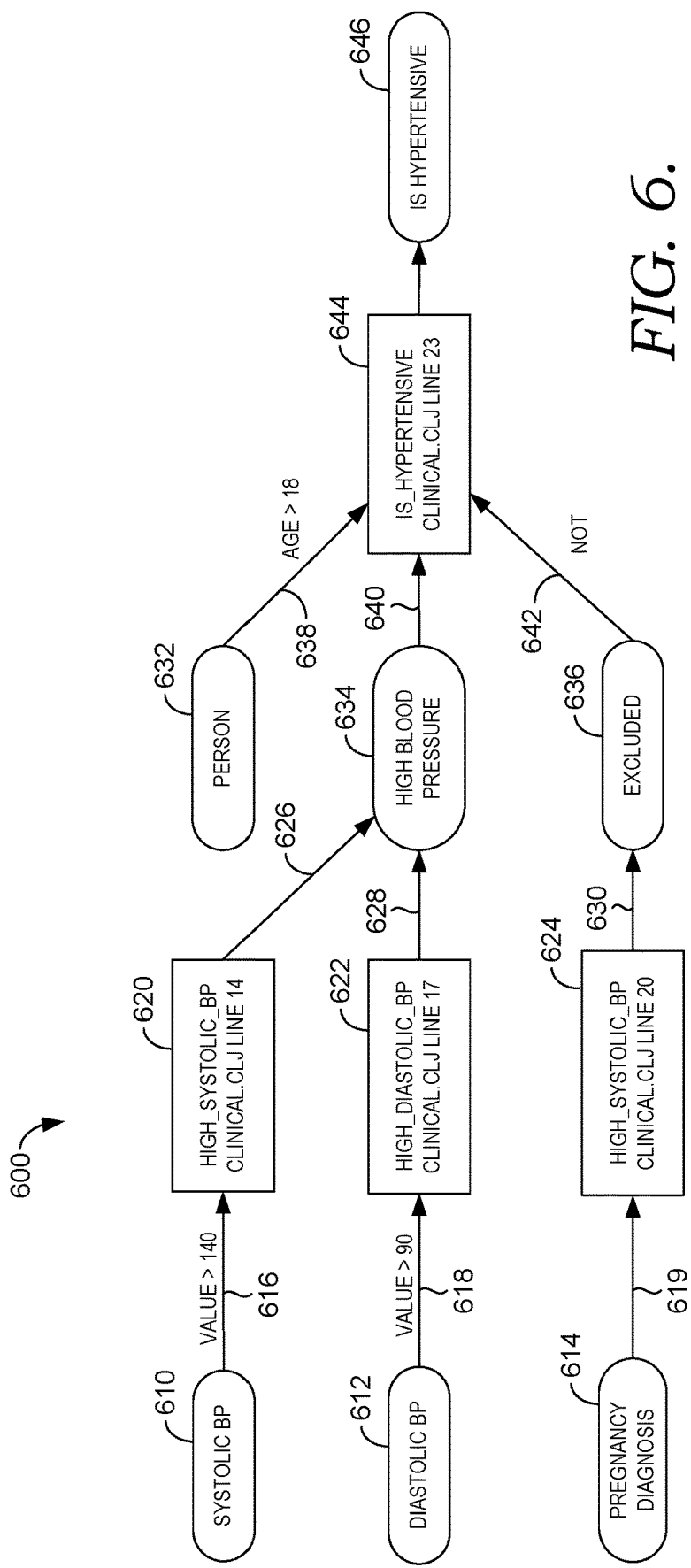
FIG. 6 depicts a visual representation of high-level clinical logic in accordance with an embodiment of the present invention.

FIG. 6 depicts a visual representation of the logic that generally follows Examples 3, 4 and 5 and is referenced generally by the numeral 600. FIG. 6 includes a set of concepts 610, 612, and 614 that may be generated using, for example, concept grouping system logic as described above with respect to, for example, Example 1. Arrows 616, 618, and 619 indicate a set of rules applied respectively to the concept 610, the concept 612, and the concept 614 to generate a first set of results 620, 622, and 624. Additional rules 626, 628, and 630 may be applied to the results 620, 622, and 624 to define additional concepts. For example, high systolic blood pressure and high diastolic blood pressure are grouped together to generate the concept "High Blood Pressure" 634. On the other hand, the result 624 "Exclude_pregnancy" is linked to the "Excluded" concept 636. A new concept, "Person," 632 is brought in at this point. Rules 638, 640, and 642 are applied to the concepts 632, 634, and 636 to define a hypertensive patient population segment, "Is_Hypertensive" 644, which, in turn, can be linked to the concept "IsHypertensive" 646. The concept "IsHypertensive" 646 may be further utilized by downstream logic.

As seen in the visual representation 600, references to specific clinical logic lines are shown thereby creating an implicit audit trail that enables the logic editor to easily follow the flow of the logic 320 in order to determine why a particular patient was included within the hypertension population segment. As well, references to specific clinical logic lines are useful for troubleshooting errors. The visual representation 600 is editable and searchable enabling the logic editor to edit, find, delete or add information.

Returning to FIG. 3, the output of the batch processing nodes 310, 312, 314, and 316 is outcome data 340 stored in the outcome data store 340. Depending on the logic 320 executed, the outcome data 340 may include members of a population identified to be eligible for one or more health intervention programs, a stratification of the identified members based on degree of risk, condition-specific recommendations, and data related to monitoring the health of identified members to determine if the members' health is stable, declining, or improving while enrolled in the program(s). The outcome data 340 may be available to healthcare facilities, such as the healthcare facilities 212, 216, and 220 of FIG. 2, to assist those facilities in managing the health of the population segments serviced by the facilities. As well, the outcome data 340 may be used for analytics, patient registries, and the like.

As mentioned, the runtime engine 309 further includes the incremental processing nodes 324, 326, 328, and 330 of which the incremental processing node 324 will be used as a representative example. The incremental processing node 324 includes a processor 332 executing high-level clinical logic 334, and a memory cache 336. The logic 334 is the same as the logic 320 used by the batch processing node 318. The incremental processing node 324 generally subscribes to health data updates associated with one or more specified patients. Updates are streamed in real time to the incremental processing node 324 via the synchronization process as the updates occur. Once an update is received, the incremental processing node 324 processes the update using the logic 334.

The cache 336 stores portions of a patient's electronic medical record that are pertinent to the execution of the logic 334. The cache 336 may be emptied if no active updates for the patient are received and/or if the incremental processing node 324 is running low on memory. If an update is subsequently received for the patient, the pertinent portions of the patient's electronic medical record are re-loaded from the distributed storage 322 as shown by arrow 338.

Outcome data 340 is generated by the incremental processing nodes 324, 326, 328, and 330. Like above, the outcome data 340 may include members of a patient population who qualify for one or more health intervention programs, a stratification by degree of risk of the identified members, condition-specific recommendations, and monitoring data related to the identified members.

Although use of the high-level clinical logic has been discussed in terms of a parallel processing architecture, it is contemplated that the high-level clinical logic may also be utilized in simple service calls relating to a single patient. For example, an application may be configured to receive a clinician request directed towards determining if a certain patient qualifies for enrollment in a hypertension program. The application can execute the high-level clinical logic against the patient's data to determine if the patient qualifies for the program. Any and all such aspects, and any combination thereof, are contemplated as being within the scope of the invention.

Turning now to FIG. 4, a flow diagram is shown of an exemplary method 400 of identifying members of a population who qualify for health intervention programs. Types of intervention programs are numerous, but representative examples may include hypertension management programs and diabetes management programs. At a step 410, patient population health data is received by a runtime engine (such as the runtime engine 309 of FIG. 3) from one or more data sources, such as the healthcare facilities 212, 216, and 220 of FIG. 2. Prior to being received from the healthcare facilities, the patient population health data is generally stored in association with electronic medical record systems associated with the healthcare facilities and includes such information as lab results, clinical notes, procedure results, medication orders, peripheral device readings, and the like for patients serviced by the healthcare facilities. The patient population health data may be received in multiple, disparate formats depending on the underlying characteristics of the electronic medical record systems that store the information.

At a step 412, the received patient population health data is stored in association with a distributed storage system such as the distributed storage 322 of FIG. 3. As explained above, the storage is distributed across a plurality of batch processing nodes, and each storage system generally stores a complete, historical electronic medical record of one or more specified patients. In one aspect, prior to storing the data in the distributed storage system, the data is minimally processed to convert the raw data into standardized structures which are further translated into high-level concepts using concept mapping and concept grouping system logic.

At a step 414, batch processing nodes, such as the batch processing nodes 310, 312, 314, and 316 of FIG. 3, execute a high-level clinical logic against the patient population health data in order to identify members of the population who qualify for one or more health intervention programs. For example, high-level clinical logic may be used to identify members of the population who are at risk for or qualify for a hypertension management program administered by a healthcare facility. Additional high-level clinical logic may be used to stratify members within the identified segment based on degree of risk, or to monitor health metrics of identified members in order to determine if the management program is effective.

As explained above, the high-level clinical logic is a healthcare-domain specific declarative language that utilizes high-level concepts to describe data of interest. The high-level clinical logic operates independently of the underlying data format allowing it to be de-coupled from existing data formats and pushed out to multiple processing nodes acting in parallel in order to process large amounts of data. Further, because the logic views code as data, the logic can be visually represented on a graphical user interface. A user, such as a clinician, is able to edit the logic on the user interface. For instance, the user can add, remove, and edit logic descriptions. The logic is also searchable so that the user can find specific pathways. Further, branches may be collapsed and hidden from view to simplify searching. A natural consequence of this logic feature is that the visual representation implicitly depicts an audit trail which may be useful for trouble-shooting or determining why a particular patient was included within a particular program.

Turning to FIG. 5, FIG. 5 depicts a flow diagram of an exemplary method 500 of managing population health. At a step 510, patient population health data is received from one or more electronic medical records systems associated with one or more healthcare facilities. At a step 512, the patient population health data is stored in association with a distributed storage system that is physically coupled to a plurality of batch processing nodes acting in parallel.

At a step 514, updates to the patient population health data are received by one or more incremental processing nodes, such as the incremental processing nodes 324, 326, 328, and 330 of FIG. 3, of a runtime engine. Each incremental processing node subscribes to updates relating to one or more specified patients. Further, each incremental processing node maintains a memory cache. Patient information that facilitates execution of the high-level clinical logic (e.g., provides context to the clinical logic) is maintained in the memory cache. If no recent updates are received for a patient and/or if memory is running low on the incremental processing node, the memory cache may be dumped. If, however, new data is received for the patient, the cache may be re-loaded from the distributed storage system associated with the batch processing nodes.

At a step 516, a high-level clinical logic is executed against the patient population health data and the updated information to, among other things, identify members of a population who qualify for one or more health intervention programs. Each batch processing node and each incremental processing node has an associated processor (e.g., the processor 318 and the processor 332 respectively of FIG. 3) that executes the high-level clinical logic. Other outcome data resulting from the execution of the logic may include stratification data based on degree of risk, and monitoring data.

While embodiments of the present invention have been described in relation to executing high-level clinical logic against patient population health data to identify people who qualify for a health intervention program, embodiments will not be described as to how the high-level clinical logic is generated.

In one embodiment, a document that is readable and easily understandable by humans may be converted or translated into a machine-readable document, such as computer-readable code that comprises high-level clinical logic. Below is an example of a simplified document that is in human-readable form. This document shown in Example 6 below is an example of an advertisement for a diabetes management program for people who meet specific criteria.

---
Program: Diabetes Management (Example 6)
This is a diabetes management program. . .
Inclusion Criteria:
    Age range: 18-75
    One of the following conditions:
    Diabetes diagnosis
    Using insulin medications
    ...
Measures:
    HbA1c < 8
    Nephropathy Monitoring
    ...

---

Various words or phrases may be identified from the human-readable document provided above that can be used to generate the computer-readable code. For instance, one or more concepts and one or more concept-specific functions may be identified from the document, and may be defined based on data in the document. In one embodiment, concepts are nouns that define, for exemplary purposes only, a treatment, an illness, or a disease. A concept-specific function may be, for example, an action or a verb that is associated with a concept. In some instances, the concept-specific function may not be a verb, but may define a condition for a concept to be true. For instance, exemplary concept-specific functions include days-since, age-as-of-date, date-between, clinical-value, most-recent-value, age-between, or discard-outliers. Each of these defines a particular characteristic of a concept.

The following is a continuation of Example 6 above, and is exemplary computer-readable code that is generated from the human-readable document provided above.

---
(defprogram diabetes
"This is a diabetes management program. More doc would go here."
  (identification
    (Person (age-between?
      (age-as-of-date this @program-end-date), 18,75)
    (or (InsulinMed (date-between? this,
      @previous-year-start,
      @program-end-date))
(DiabetesCondition (date-between? this,
      @previous-year-start,
      @program-end-date))))
(measures
hba1c-lessthan8
nephropathy-monitoring))

---

The knowledge from the human-readable form document may translate directly into a program definition. Concepts and concept-specific functions may be identified and defined such that the logic can be applied to a population of members.

As shown, one or more rules may be written in computer-readable form. For instance, the following computer-readable code of Example 7 is an exemplary rule. It represents a detection of when a new checkup is needed.

---
(defrule needs-to-visit (Example 7)
"Indicate a new checkup needed if there hasn't been one for 180 days."
(LastPrimaryCareVisit [days-since (this) > 180])
=>
(insert NewCheckupNeeded))

---

The following Example 8 illustrates how concepts are utilized in logic. Here, it is determined that "insulin" is a fact that corresponds to the concept "InsulinMed."

---
(defrule get-insulin-med (Example 8)
(Medication (has-concept? drugCode "INSULIN"))
=>
(insert InsulinMed))

---

Another example of how concepts are utilized in logic is shown below in Example 9.

---
(defrule get-diabetes-condition (Example 9)
(Condition (has-concept? conditionCode "DIABETES"))
=>
(insert DiabetesCondition))

---

The following Example 10 is yet another example, but utilizes both concepts and concept-specific functions.

---
(defrule get-diabetes-condition (Example 10)
(or (InsulinMed (date-between? this, @start-date, @end-date))
(DiabetesCondition (date-between? this, @ start-date, @ end-date)))
=> (insert Diabetic))

---

In embodiments, concept-specific functions, such as days-since, are consistent across many different data types. The logic may seek days since a last visit, a screening, a vaccination, or many other pieces of knowledge, although each may be represented in greatly different ways. The use of polymorphic functions allows us to define a days-since function and transparently call the correct implementation for the data type at hand. As new data types arrive, new days-since implementations may be added to meet those needs as well. As such, regardless of the data type, the concept-specific functions will be able to work consistently, regardless of the data type. For example, below illustrates how the same concept-specific function is used with different data types: systolic blood pressure and lab results.

(discard-outliers SystolicBP)
(discard-outliers LabResults)

Additionally, the following functions illustrate usage consistently across data types.

(days-since AnnualPhysical)
(days-since NephropathyScreening)
(days-since LabTest)

Measures may be defined similarly to programs, using the same underlying vocabulary. Examples 11 and 12 below define a measure and the criteria needed for them to be met, or satisfied.

```
(defmeasure hba1c-lessthan8                    (Example 11)
(display "Hba1c < 8")
(met
(NewestHba1cResult [clinical-value (this) < 8])))
(defmeasure nephropathy-monitoring             (Example 12)
(display "Medical Attention for Nephropathy")
(met
(NephropathyScreening (date-between? (clinical-timestamp this),
@previous-year-start,
@program-end-date)))
(met
(NephropathyEvidence (date-between? (clinical-timestamp this),
@previous-year-start,
@program-end-date))))
```

The following rule utilizes a measurement of Hba1c, as shown in Example 13 below.

```
(defrule hba1c-lessthan8                       (Example 13)
(ProgramIdentification [name = diabetes])
(NewestHba1cResult[clinical-value (this) < 8])
=>
(insert MeasureOutcome diabetes hba1c-lessthan8 :outcome-met))
```

Other embodiments are directed to notifying people in a population who are at risk of a particular complication or align them with certain care providers. For instance, suppose a hospital, insurance company, or other medical care provider wants to contact people who did not meet a specific measure and have not seen a specialist in 90 days. This logic can be placed in its own ruleset, building on the example provided above. One such rule could be similar to Example 14 below. This example uses a MeasureOutcome produced by a program execution. This shows how the system is composable, taking value from one unit and easily leveraging it in another, without needing to worry about how a given outcome was inferred. Additional rulesets may be added, building on top of others.

```
(defrule plan-endocrinologist-visit            (Example 14)
(MeasureOutcome [program = diabetes and
measure = hba1c-lessthan8 and
status = :outcome-not-met])
(not (Visit [type = :endocrinologist and days-since (this) < 90]))
=>
(insert EndocrinologistVisitNeeded))
```

Figure 7:
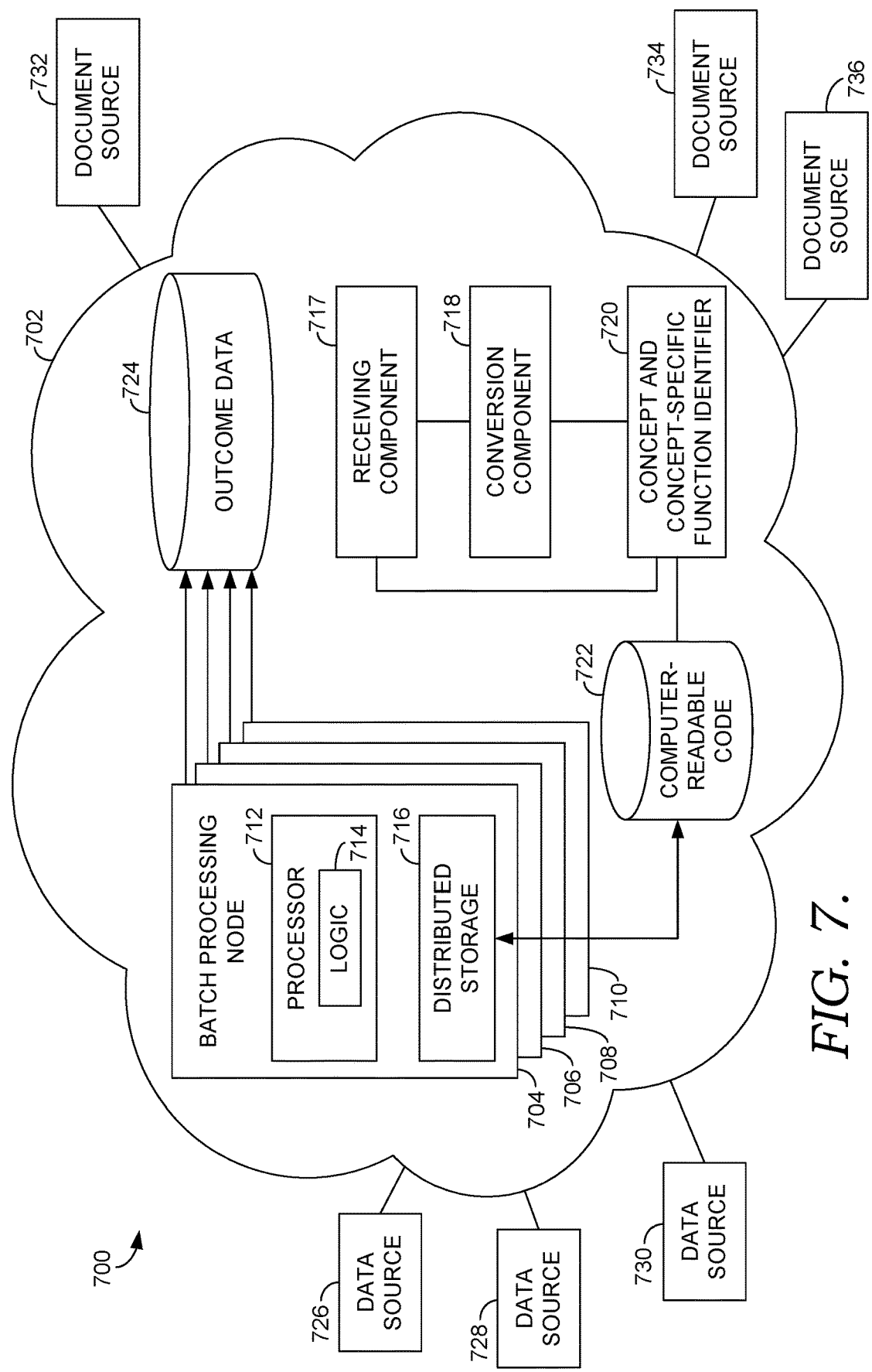
FIG. 7 is a block diagram of an exemplary system for, among other things, generating computer-readable code from a human-readable document to identify members of a population who qualify for a health intervention program suitable to implement embodiments of the present invention.

FIG. 7 is a block diagram of an exemplary system, referred to generally as item 700, for, among other things, generating computer-readable code from a human-readable document to identify members of a population who qualify for a health intervention program suitable to implement embodiments of the present invention. The embodiment of FIG. 7 includes many of the same aspects as FIG. 3, described herein, and as such, the aspects that are the same will not be described in detail in relation to FIG. 7. Generally, FIG. 7 depicts a detailed view of the runtime engine 228 of FIG. 2, now labeled item 702 of FIG. 7. Initially, the runtime engine 702 includes a receiving component 717, a conversion component 17, a concept and concept-specific function identifier 720 (hereinafter the concept identifier 720), and a database for storing computer-readable code 722. Initially, one or more document sources, shown as document sources 732, 734, and 736, provide one or more documents in human-readable form to the runtime engine 702. The document source may be one of any number of sources, including medical-related journals, magazine articles, press releases, or any other publication. The document provided may be associated with an upcoming clinical trial, may include general health information, or some other document that includes conditions to be met for something to occur. For instance, in one embodiment, the document is similar to the document provided above in Example 6, such that it for a healthcare program in diabetes management, and includes inclusion criteria and measures that must be met for a person to quality for the program. Many other examples of documents, even non-healthcare related documents, are contemplated to be within the scope of the present invention.

The receiving component 717 is operable to receiving one or more sets of patient population health data from one of the data sources 726, 728, or 730, and also to receive a document in human-readable from one of the document sources 732, 734, or 736. In one embodiment, the receiving component 717 may not be responsible for receiving the patient population health data, but may just be responsible for receiving the documents from the document sources 732, 734, and 736. As mentioned, the documents received are in a form that is clear and understandable to a human. In one embodiment, the document received is not in computer-readable form.

The conversion component 718 utilizes the concept identifier 720 to generate computer-readable code, which is stored in the database 722. In one embodiment, the conversion component 718 is not a separate component from the concept identifier 720, and instead the two components are integrated. The concept identifier 720 is operable to identify, from the received document, one or more concepts and one or more concept-specific functions associated with the concepts. The concept identifier 720 may also define the concepts and concept-specific functions based on data in the received document. For example, using Example 6 provided above, the criteria of an age range of 18-75 may be identified as a concept-specific function that can be translated into computer-readable code reading (Person (age-between? (age-as-of-date this @program-end-date), 18, 75). Another example of an identified concept-specific function in a document may be to determine how many days since the patient's last annual physical. When converted to computer-readable code, this may read as (days-since AnnualPhysical). For the identification of a concept, an example may be the identification of patients who have diabetes, for instance. Logic representing this rule may read (defrule get-diabetes-condition (Condition (has-concept? conditionCode "DIABETES"))=>(insert (DiabetesCondition)).

Once the concepts and concept-specific functions are identified, the conversion component 718 is able to convert the document in human-readable form to computer-readable code. As such, the conversion component 718 is operable to generate computer-readable code that corresponds to the received document utilizing the defined concepts and concept-specific functions. The computer-readable code comprises a set of high-level clinical logic.

The runtime engine 702, in the embodiment of FIG. 7, also includes a plurality of batch processing nodes (items 704, 706, 708, and 710). While there may be more than one batch processing nodes, the discussion herein will refer to batch processing node 704, but will apply equally to other batch processing nodes, such as items 706, 708, and 710. Batch processing node 704 includes a processor 712 executing a high-level clinic logic 714 and distributed storage 716. The batch processing node 704 receives the computer-readable code 722 and is operable to execute the high-level clinical logic 714 contained therein against patient population health data to identify members of the population who qualify for the health intervention program. As such, inputs to the runtime engine include patient population data and human-readable documents, while the output may be one or more members of the population who qualify for a health intervention program. The outcome data is stored in outcome data store 724.

Figure 8:
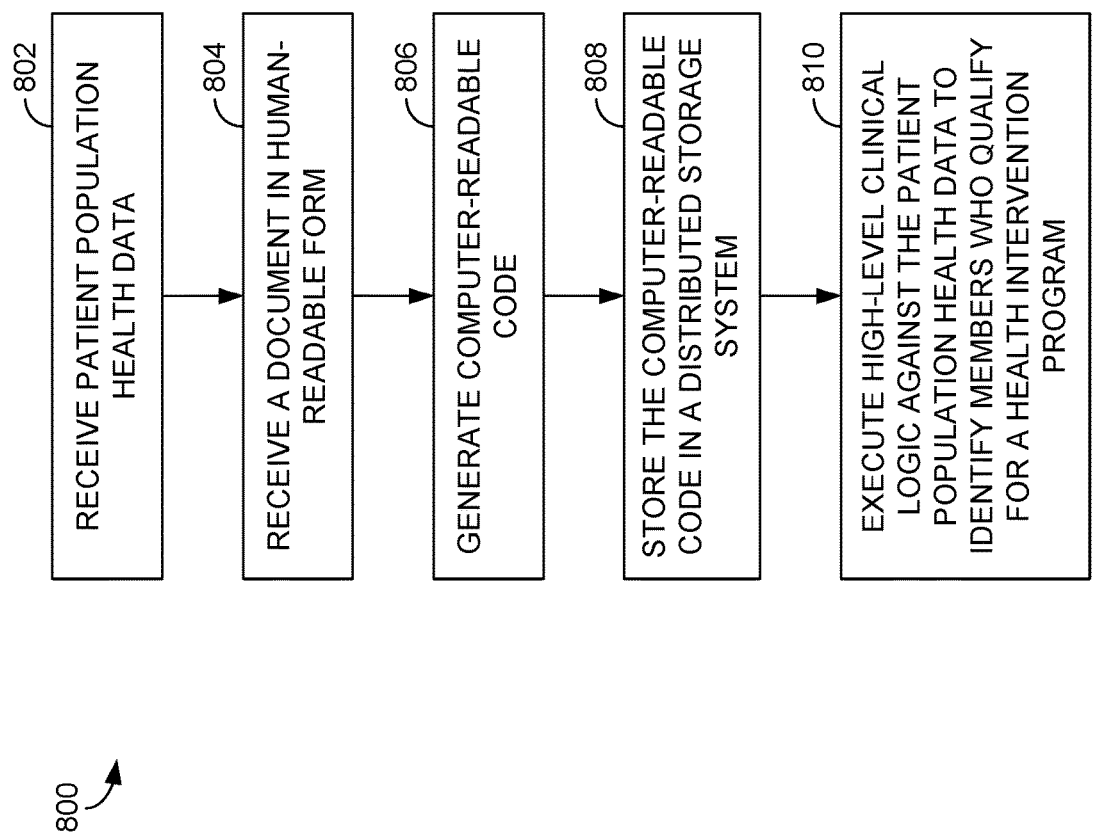
FIG. 8 is a flow diagram of an exemplary method of identifying members of a population who qualify for a health intervention program using computer-readable code generated from a document in human-readable form, in accordance with an embodiment of the present invention.

Turning now to FIG. 8, FIG. 8 is a flow diagram of an exemplary method 800 of identifying members of a population who qualify for a health intervention program using computer-readable code generated from a document in human-readable form, in accordance with an embodiment of the present invention. Initially at step 802, patient population health data is received. In one embodiment, this data is received from electronic medical records (EMR) systems associated with one or more healthcare facilities. A document in human-readable form is received at step 804. In one embodiment, the document corresponds to a health intervention program, such as a diabetes management program, a clinical study, etc.

At step 806, computer-readable code is generated that, in one embodiment, corresponds to the received document in human-readable form. The computer-readable code comprises high-level clinical logic that defines rules that are to be applied to patient data. In embodiments, the computer-readable code is generated by identifying concepts and concept-specific functions from the human-readable document. The concepts and concept-specific functions are defined based on data in the document. For exemplary purposes only, concept-specific functions may include one or more of days-since, age-as-of-date, date-between, clinical-value, most-recent-value, age-between, or discard-outliers. Many other concept-specific functions exist and are contemplated to be within the scope of the present invention. Further, in one embodiment, the computer-readable code is automatically generated from the received document, and is generated without user intervention, such that a user is not actually reading the document and identifying the concepts and concept-specific functions. Instead, a computer device is performing this function without manual steps.

At step 808, the computer-readable code is stored in a distributed storage system. The high-level clinical logic is executed at step 810 against the patient population health data to identify members who qualify for a health intervention program.

Figure 9:
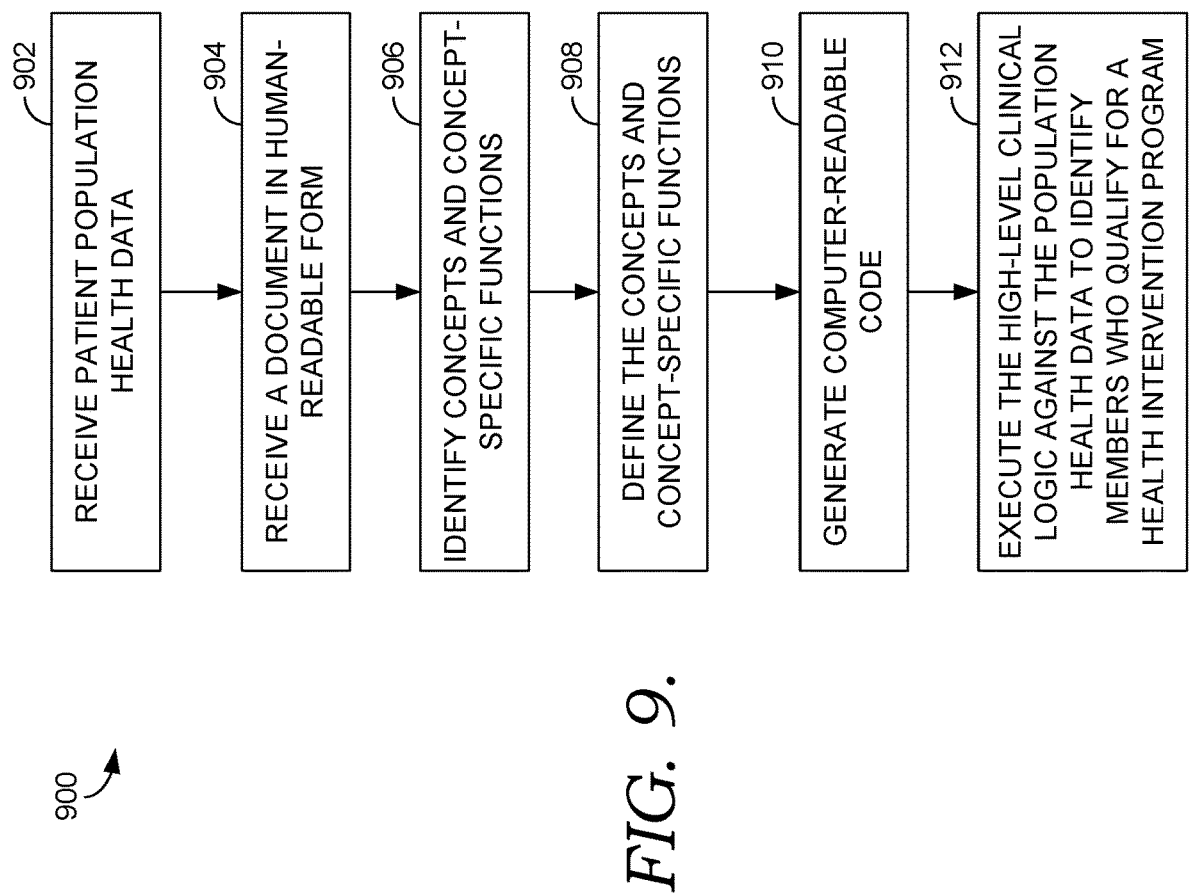
FIG. 9 is a flow diagram of another exemplary method of identifying members of a population who qualify for a health intervention program using computer-readable code generated from a document in human-readable form, in accordance with another embodiment of the present invention.

Referring to FIG. 9, a flow diagram is depicted of another exemplary method 900 of identifying members of a population who qualify for a health intervention program using computer-readable code generated from a document in human-readable form, in accordance with another embodiment of the present invention. At step 902, patient population health data is received, and at step 904, a document is received, the document being in human-readable form. One or more concepts and one or more concept-specific functions are identified at step 906. At step 908, the concepts and concept-specific functions are defined based on data in the received document. At step 910, computer-readable code is generated, the code corresponding to the received document. The code may be generated utilizing the defined concepts and concept-specific functions. Further, the code comprises a set of high-level clinical logic. At step 912, the high-level clinical logic is executed against the population health data to identify members who qualify for a health intervention program. In embodiments, the health intervention program is one or more of better-managed care, an opportunity for improvement in care of one or more members of a population, a recommendation relating to healthcare of the patient, a clinical trial, or an incentive. In one embodiment, the document may directly correspond to the health intervention program.

As previously discussed, embodiments of the present invention have been described in relation to executing high-level clinical logic against patient population health data to, for example, identify patients who qualify for a health intervention program. Additionally, embodiments of the present invention have been described in relation to generating high-level clinical logic by identifying concepts and concept-specific functions in a human-readable document and converting these concepts and concept-specific functions into computer-readable code. Embodiments will now be described for generating and executing high-level clinical logic that provides explainability to an end-user, such as a clinician, for why a particular patient in a patient population qualifies or does not qualify for a particular health intervention program.

Typically, when a patient fails to qualify for a health intervention program, the clinician caring for the patient is left wondering the reason for the disqualification. The clinician may attempt to go back through the patient's records in order to pinpoint what item with respect to the patient's record triggered the disqualification. In order to do this, the clinician is required to understand all the criteria that must be met for a particular patient to qualify for the program. This places an unnecessary burden on the clinician. Additionally, manually combing through the patient's records wastes the clinician's time and becomes prohibitive when the clinician is caring for a large number of patients and a substantial proportion of them fail to qualify for the program. Another alternative is for the clinician to contact the third-party vendor who is managing the software for the health intervention program and request that the vendor supply the information for why the patient was disqualified. This also wastes valuable clinician resources, degrades the clinician's confidence in the third-party vendor, and raises the vendor's support costs which are ultimately passed down to the clinician. By providing the clinician with an easy-to-understand explanation for why the patient did not qualify for the program, the clinician is able to route his/her resources to the important task of patient care.

Providing explainability to an end-user is accomplished by generating a set of high-level clinical logic rules that are executed against the patient population health data to determine precisely why a particular patient fails to qualify for a health intervention program. These "explainability" rules are generated from and run on top of the already-existing high-level clinical logic that is used to, for example, identify patients who qualify for a particular program. The outcomes of these explainability rules are subsequently structured into a usable form by a result interpreter and are provided to an end-user such as a clinician in an easy-to-understand format.

As described above with respect to, for instance, Example 3, high-level clinical logic may be used to identify patients who qualify for particular health intervention program such as, for example, a diabetes management program, a hypertension management program, an asthma management program, and the like. To identify patients who qualify for a particular program, the high-level clinical logic may string together components using logical operators (AND, OR, NOT, etc.) to generate a component expression, although a single component by itself may be sufficient to determine whether a patient qualifies for a health intervention program. For example, a component expression may comprise: If (A OR B) and C and (NOT D) then: Recommend Program X. Each variable in this expression represents a component. As used with respect to this embodiment, a component may be defined as a clinical measure expressed in high-level clinical logic. Examples of clinical measures are numerous but representative examples may include, for example, clinical result values, allergies, medications, visit records, and the like.

Each component is characterized or defined by one or more sub-criteria, and taken together a component's sub-criteria express a cohesive unit of clinical logic. In order for a component to be satisfied or met, the patient population health data against which the component is executed must satisfy each of the component's sub-criteria. To aid in the discussion below, an exemplary component, "HbA1C" will be used. The HbA1C component describes the clinical measure "HbA1C test" or glycated hemoglobin test which is a blood test used to determine how well a person's diabetes is being controlled. The HbA1C component may be used by itself to determine whether a particular patient is eligible or qualifies for a diabetes management program. Alternatively, the HbA1C component may be combined using logical operators with other components to generate a component expression used to determine if a patient qualifies for the diabetes management program. For example, a component expression that may be used to determine if a patient qualifies for a diabetes management program may comprise: if (HbA1C >8 AND BMI >30) OR HbA1C >9 AND NOT Pregnant then: Recommend diabetes management program.

A first exemplary component sub-criteria is a selection sub-criteria that specifies a subset of the patient population health data that is relevant to the component. With respect to the HbA1C component, the selection sub-criteria may specify that HbA1C data items within the patient population health data are of interest. Another exemplary component sub-criteria comprises a value sub-criteria that specifies or indicates a value parameter or value range for the clinical measure represented by the component. Using the HbA1C component example, the value sub-criteria may specify "HbA1C<8.0" to indicate that patient HbA1C test values less than 8.0% are needed to satisfy the component. Depending on the clinical measure represented by the component, other value parameters may comprise "exists," or "null." For example, if a component's selection sub-criteria is documented mammogram results, then the value parameter of "exists" would be satisfied by the presence of a mammogram result in the patient's electronic medical record.

Continuing, another component sub-criteria comprises a date sub-criteria that specifies a date or date range for the clinical measure represented by the component. For the HbA1C component, for example, the date sub-criteria may indicate that a HbA1C test be documented within the past year. The date sub-criteria may comprise an open-ended range when, for example, the clinical measure represented by the component is whether a patient has ever had a test, procedure, or the like. Yet another component sub-criteria comprises a cardinality sub-criteria that specifies a minimum number of data items that meet the selection sub-criteria needed within the patient population health data. For example, the cardinality sub-criteria for the HbA1C component may specify that each patient must have at least two documented HbA1C test results in his/her patient population health data.

As mentioned, taken together a component's sub-criteria express the high-level clinical logic for the component. A component may comprise all four of the sub-criteria described above, or alternatively, a component may include one sub-criteria, two sub-criteria, or three sub-criteria. Each of the component's sub-criteria should be satisfied by the patient population health data in order for the component to be satisfied. Again, using the HbA1C component example, the HbA1C component is satisfied if at least two documented HbA1C test results exist for a patient in the patient's population health data, one of the test results was documented in the past year, and this test result indicates that the HbA1C value for the patient was less than 8.0.

If one or more of a component's sub-criteria are not met by a particular patient's population health data, then the component is not satisfied. The present embodiment is directed to, in part, generating high-level clinical logic rules (also known as "explainability rules") for each component that are designed to identify which of the component's one or more sub-criteria is not met or satisfied by a particular patient's population health data. Because these explainability rules are permutations of the already-existing high-level clinical logic rules designed to identify patients who qualify for health intervention programs, the financial and time resources needed to generate these rules are minimized thus helping to keep third-party vendor support costs down which ultimately benefits the end-user.

Using the HbA1C component as a representative example, the generation of explainability rules for this component will be illustrated by using a number of examples of computer-readable code. First, the high-level clinical logic rule to identify patients who satisfy the HbA1C component may be defined in Example 15 as:

```
defrule hba1c_8:                                        (Example 15)
support = HbA1c (value > 8.0) AND (date in date_range)
then:
insert ComponentResult (result = MATCH, component = "hba1c_8.0", support)
```

Permutations of this rule are then generated to identify which of the HbA1C component's sub-criteria is not satisfied by a patient's population health data. For example, an explainability rule to identify that the HbA1C's value sub-criteria is not met can be represented by the following computer-readable code of Example 16:

```
defrule hba1c_8_value_out_of_range:                     (Example 16)
NOT ComponentResult (result = MATCH, component = "hba1c_8.0")
AND
support = HbA1c (date in date_range)
then:
insert ComponentResult (result = VALUE_OUT_OF_RANGE, component =
"hba1c_8.0, support)
```

The outcome of Example 16 is the result VALUE_OUT_OF_RANGE. Additionally, the outcome of Example 16 includes any facts (e.g., clinical values) supporting the VALUE_OUT_OF_RANGE outcome. For example, the supporting fact may include the actual value of the HbA1C even though it is out of the designated range.

An explainability rule to identify that the HbA1C's date sub-criteria is not met can be represented by the following computer-readable code of Example 17:

```
defrule hba1c_8_not_in_date_range                       (Example 17)
NOT ComponentResult (result = MATCH, component = "hba1c_8.0")
AND
NOT ComponentResult (result = VALUE_OUT_OF_RANGE, component =
"hba1c_8.0")
AND
support = HbA1c
then:
insert ComponentResult (result = DATE_OUT_OF_RANGE, component =
"hba1c_8.0", support)
```

The outcome of Example 17 is the result DATE_OUT_OF_RANGE. Additionally, the code of Example 17 generates facts supporting the outcome DATE_OUT_OF_RANGE. For example, the date when the last HbA1C blood test was documented may be provided along with the test value.

Similar explainability rules can be generated to identify that, for example, no matching data items exist for a particular component within a patient's population health data (e.g., the selection sub-criteria is not met), and/or that there are not a sufficient number of data items present in the patient's population health data for a particular component (e.g., the cardinality sub-criteria is not met).

To summarize, it is contemplated that at least four outcomes can be generated by the explainability rules depending on which of a component's sub-criteria is not satisfied. A VALUE_OUT_OF_RANGE outcome is generated when the value sub-criteria is not met which may occur, for example, when a data item for a patient exists, is within the specified date range, but it is above or below the desired value parameter or value range. A NO_MATCHING_DATUM outcome may be generated when the selection sub-criteria is not met such as when a patient's population health data does not include any data items specified by the selection sub-criteria. An OUT_OF_DATE_RANGE outcome may be generated when the date sub-criteria is not met which may occur, for instance, when matching data items exist in a patient's health data, but they are out of the specified date range. An INSUFFICIENT_CARDINALITY outcome may be generated when matching data items exist in a patient's health data, but there are not enough data items present to satisfy the cardinality sub-criteria. Each of the outcomes described may include supporting facts (e.g., test values, dates when the tests were documented, number of data items present, and the like). More than one outcome result may be generated for a particular component when, for example, two or more of the component's sub-criteria are not met. By way of illustrative example only, an INSUFFICIENT_CARDINALITY outcome and an OUT_OF_DATE_RANGE outcome may be generated for the same component.

As will be explained more fully below, a result interpreter component can be utilized to examine the explainability rules outcomes for each component including the supporting facts, synthesize the outcomes for a particular component and/or for a component expression, and structure the outcomes in a usable form for applications or other systems. For instance, the result interpreter may structure the outcome data in an easy-to-understand textual format that is presented on a user interface associated with an end-user such as a clinician caring for a patient, thereby providing the clinician exposure to the particular reasons why a patient did not qualify for a health intervention program.

Figure 10:
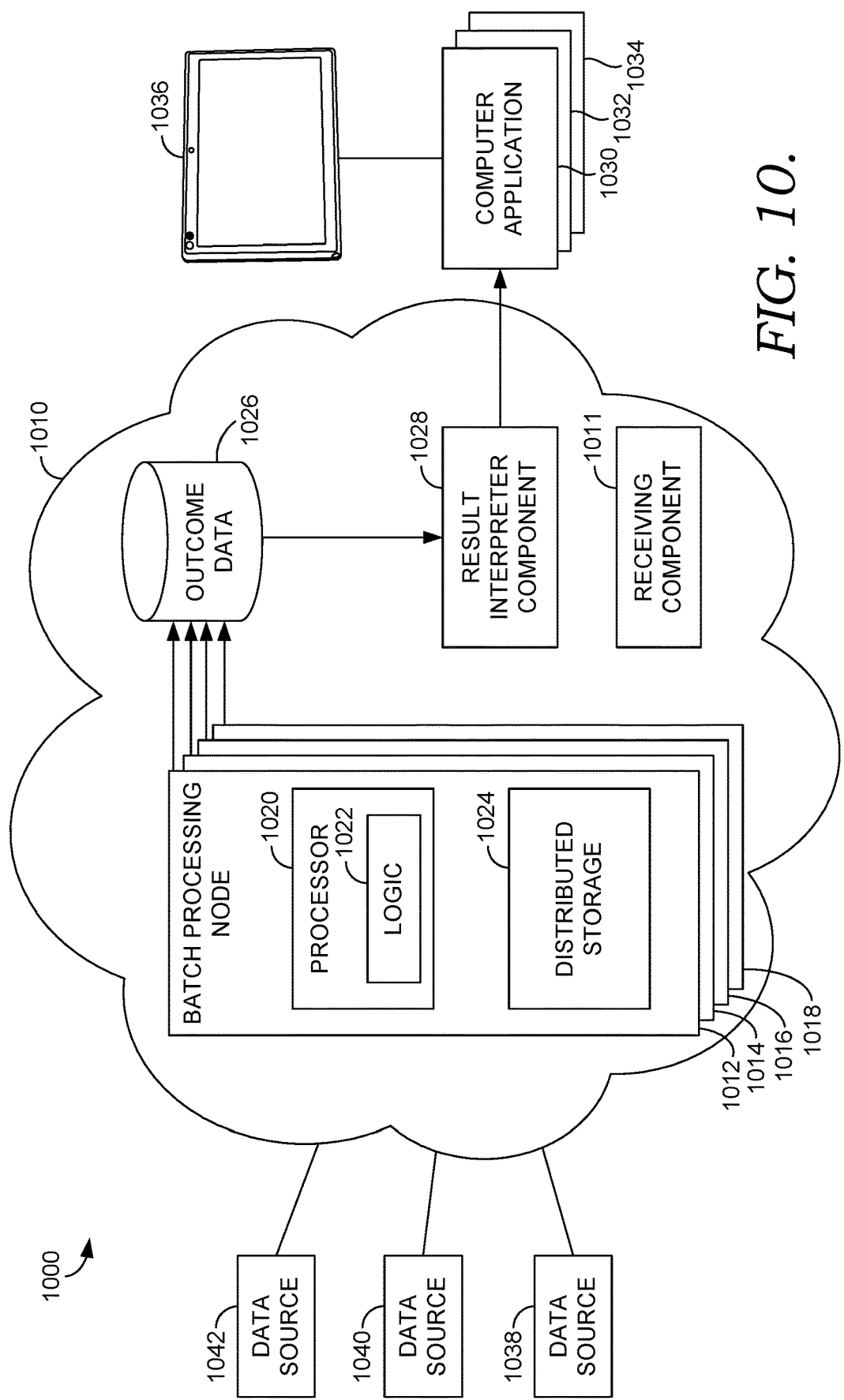
FIG. 10 is a block diagram of an exemplary system for executing high-level clinical logic explainability rules against patient population health data to identify and explain why a particular patient did not qualify for a health intervention program suitable to implement embodiments of the present invention.

Turning now to FIG. 10, FIG. 10 depicts a block diagram of an exemplary system, referred to generally by the numeral 1000, for, among other things, generating and executing high-level clinical logic explainability rules against patient population health data to identify and explain why a particular patient did not qualify for a health intervention program. The exemplary system 1000 may include the same aspects as FIGS. 3 and 7, described herein, and as such, the aspects that are the same will not be described in detail in relation to FIG. 10.

Generally, FIG. 10 depicts a detailed view of the runtime engine 228 of FIG. 2, now labeled as the runtime engine 1010 of FIG. 10. As shown in FIG. 10, the runtime engine 1010 includes a receiving component 1011 and a result interpreter component 1028. The receiving component 1011 is operable to receive one or more sets of patient population health data from one or more of data sources 1038, 1040, and 1042.

The runtime engine 1010 further includes a plurality of batch processing nodes 1012, 1014, 1016, and 1018. While there may be more than one batch processing node, the discussion herein will refer to the batch processing node 1012 but will apply equally to the other batch processing nodes 1014, 1016, and 1018. The batch processing node 1012 includes a processor 1020 that executes a high-level clinical logic 1022 and distributed storage 1024. The high level clinical logic 1022 comprises both the high-level clinical logic described above with relation to FIGS. 3 and 7 that is used to identify patients who qualify for health intervention program, and the high-level clinical logic explainability rules that are used to determine why a particular patient failed to qualify for a health intervention program.

The batch processing node 1012 receives computer-readable code, such as shown in Examples 15-17, and is operable to execute the high-level clinical logic 1022 against patient population health data to first identify patients that qualify for a particular health intervention program (using, for example, the computer-readable code shown in Example 15). If a particular patient fails to qualify for the health intervention program, the batch processing node is further operable to execute the high-level clinical logic explainability rules 1022, such as shown in Examples 16 and 17, against the patient's health data to determine why the patient failed to qualify for the program. As such, inputs to the runtime engine 1010 include at least patient population health data, while the outputs may be a first set of members of the population who qualify for a health intervention program, and a second set of members of the population who fail to qualify for the health intervention program. For both of these groups, the outputs further include explanations for why the first set of members did qualify for the health intervention program and why the second set of members did not qualify for the program including supporting facts for each set. For instance, the outcome data for those members who failed to qualify for the health intervention program includes one or more of the outcome results set forth above—OUT_OF_DATE_RANGE, INSUFFICIENT_CARDINALITY, NO_MATCHING_DATUM, and VALUE_OUT_OF_RANGE. The outcome data is stored in outcome data store 1026.

The result interpreter component 1028 is operable to act on the outcome data stored in the outcome data store 1026. More specifically, the result interpreter component 1028 is configured to structure the outcome data in a form that is usable by one or more computer applications 1030, 1032, and 1034. For each component in the clinical logic 1022, the result interpreter component 1028 analyzes the outcome results for each of the component's sub-criteria and generates a summarized description for the component. Moreover, the result interpreter component 1028 is operable to analyze the outcome results for each component's sub-criteria in a component expression and generate a summarized description for the component expression. In one aspect, the result interpreter 1028 is configured to generate a user interface, useable by the computer applications 1030, 1032, and 1034, that presents the outcome results in an easy-to-understand textual format that enables a clinician to view information relating to the criteria needed to qualify for a health intervention and why a particular patient did or did not qualify for the health intervention program. This user interface may be presented on an end-user computing device, such as end-user computing device 1036, which is utilized by a clinician in his or her practice. This will be explained in greater depth below with respect to FIG. 13.

Figure 11:
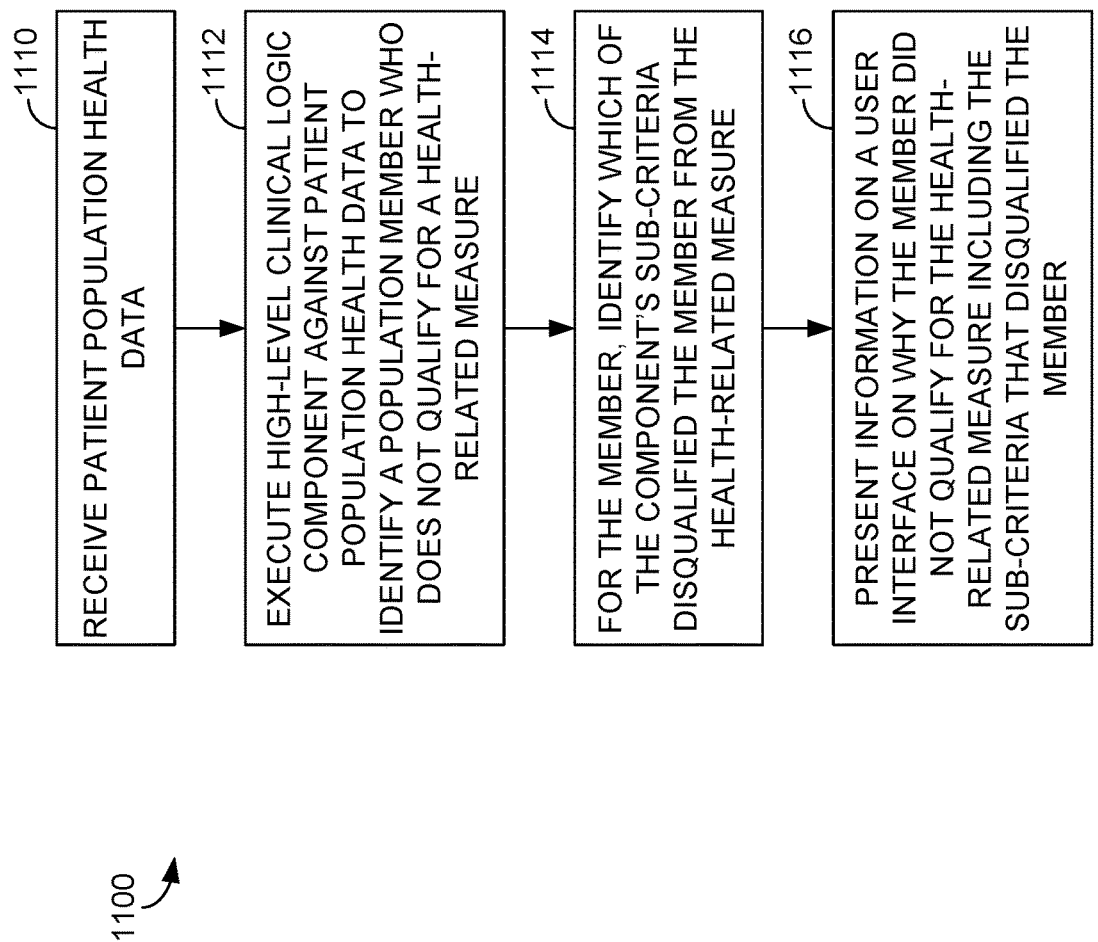
FIG. 11 is a flow diagram of an exemplary method of determining and presenting information on why members of a population do not qualify for a health intervention program in accordance with an embodiment of the present invention.

Turning now to FIG. 11, a flow diagram is depicted of an exemplary method 1100 for determining and presenting information on why members of a population do not qualify for a health intervention program. At a step 1110, one or more sets of patient population health data are received from one or more data sources such as the data sources 1038, 1040 and 1042 of FIG. 10. The data sources may be electronic medical record (EMR) systems associated with healthcare facilities.

At a step 1112, a set of high-level clinical logic is executed against the patient population health data. The high-level clinical logic (such as, for example, the high-level clinical logic shown in Example 15) may comprise logic used to identify members of the population who qualify for a particular health intervention program, and by extension, to identify members of the population who fail to qualify for the health intervention program. The high-level clinical logic comprises one or more components. If there is more than one component, the components are strung together using one or more logical operators. Each component represents a clinical measure and is defined by one or more sub-criteria. Exemplary sub-criteria may comprise a selection sub-criteria that defines the subset of the patient population health data that is relevant to the component, a value sub-criteria that specifies a value parameter or a value range for the clinical measure represented by the component, a date sub-criteria that specifies a date or date range for the clinical measure represented by the component, and a cardinality sub-criteria that specifies a minimum number of data items needed for the clinical measure represented by the component.

At a step 1114, a set of explainability rules (such as, for example, the explainability rules shown in Examples 16 and 17) is executed against patient data associated with the members who are determined not to qualify for the health intervention program in order to identify which of a particular component's sub-criteria disqualified each of the members from the health intervention program. In other words, the set of explainability rules is used to identify which of the particular component's sub-criteria are not met or satisfied by the members' health data.

At a step 1116, an indication is presented on a user interface indicating the members of the population who did not qualify for the health intervention program. For each member who failed to qualify, the indication includes information regarding the particular component and the component's sub-criteria that disqualified the member from the health intervention program. Further, the information may comprise facts supporting the disqualification. For instance, if a member fails to qualify because the member's lab value did not fall within a specified range, the disqualifying lab value will be presented on the user interface.

Figure 12:
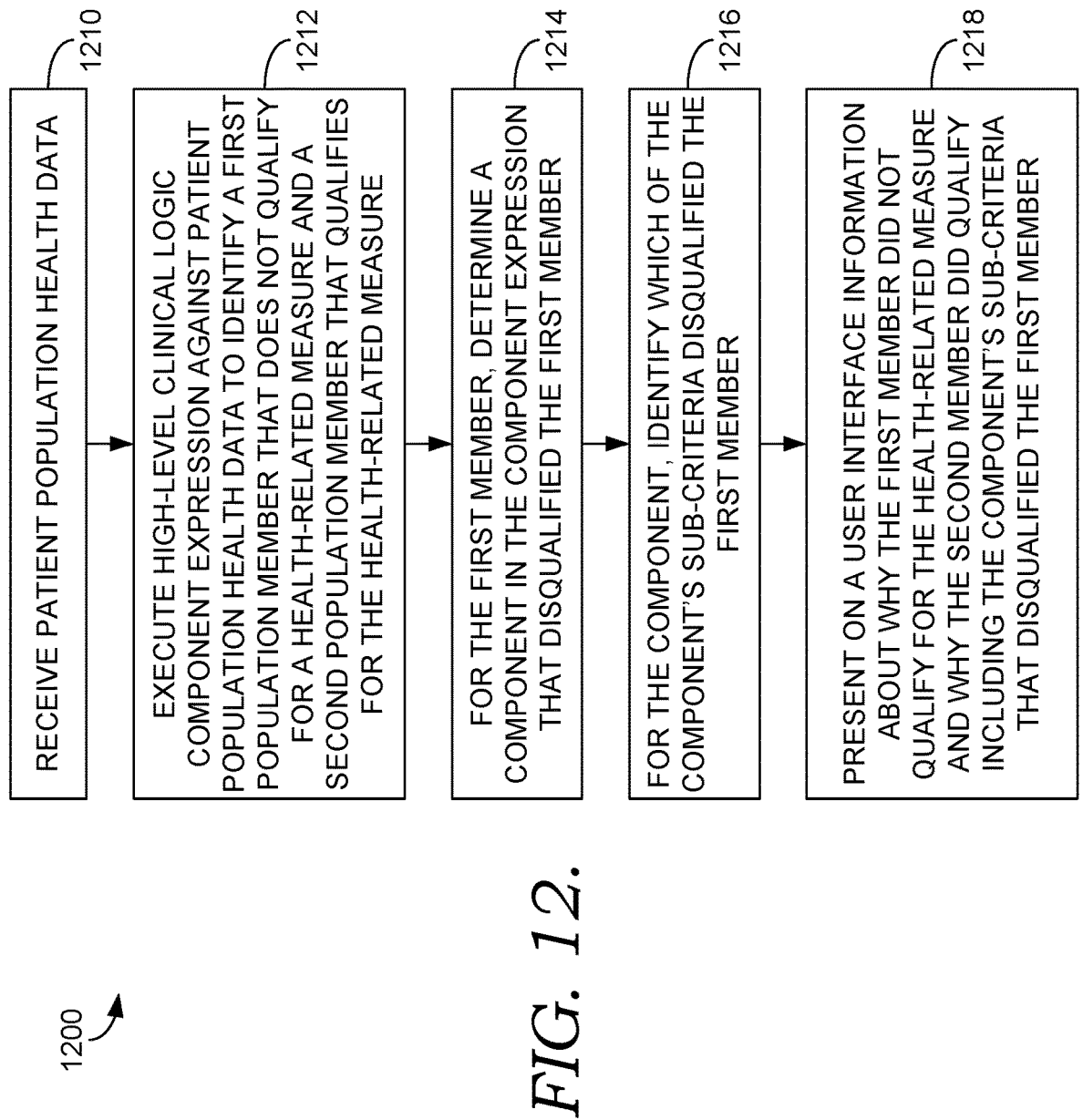
FIG. 12 is a flow diagram of an exemplary method of presenting information on determining and presenting information on why members of a population qualify and do not qualify for a health intervention program in accordance with an embodiment of the present invention.

FIG. 12 is flow diagram of an exemplary method 1200 for determining and presenting information on why members of a population qualify or do not qualify for a health intervention program. The method 1200 may be used to provide explainability for those members who fail to qualify as set out in the method 1100, but also may be used to provide explainablity for those members who do qualify. This may be useful when a clinician desires to know what criteria qualified a patient for a particular health intervention program.

At a step 1210, one or more sets of patient population health data are received by, for example a runtime engine such as the runtime engine 1010 of FIG. 10. At a step 1212, a set of high-level clinical logic is executed against the sets of patient population health data by, for example, a batch processing node such as the batch processing node 1012 of FIG. 10. The high-level clinical logic is executed against the data to identify members of the population who qualify and who do not qualify for a particular health intervention program. The high-level clinical logic in this case may comprise a component expression having one or more components coupled together using logical operators where each component in the expression is defined by one or more sub-criteria. For those members of the population who are identified as qualifying for the health intervention program, the high-level clinical logic is also used to generate supporting facts for the qualification.

At a step 1214, for those members of the population who are determined not to qualify for the health intervention program, a set of explainability rules is executed against the members' data to identify which of the components in the component expression disqualified a particular member from the health intervention program, and, at a step 1216, for those components that disqualified the member, to identify which of the component's sub-criteria disqualified the member from the health intervention program. The explainability rules are further configured to generate clinical facts supporting the disqualification.

At a step 1218, information is presented on a user interface associated with an end user such as a clinician providing care to one or more members of the population. For a member that did qualify for the health intervention program, the information may comprise an indication that the member qualified, information on the components in the component expression used to determine that the member qualified, information on each of the components' sub-criteria, and supporting clinical facts.

For a member that did not qualify for the health intervention program, the information may comprise an indication that the member did not qualify, information on the component or components that disqualified the member, information on which of the component's sub-criteria disqualified the member, and clinical facts supporting the disqualification.

Figure 13:
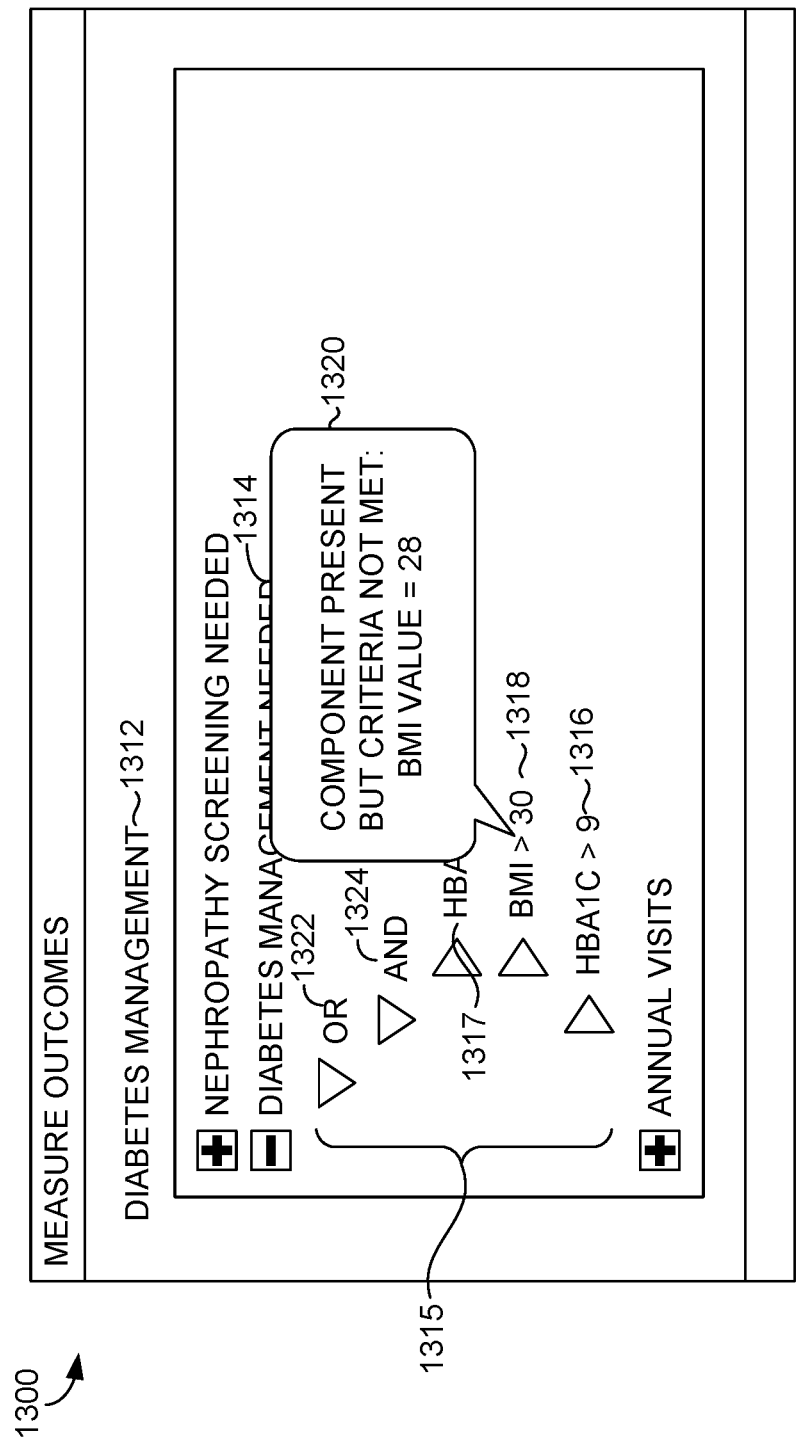
FIG. 13 is an exemplary graphical user interface for presenting information on why members of a population qualify and do not qualify for a health intervention program in accordance with an embodiment of the present invention.

Turning now to FIG. 13, an exemplary user interface (UI) 1300 is depicted illustrating how explainability is provided to an end user, such as a clinician, on why a particular patient did not qualify for a health intervention program. The UI 1300 includes an indication of a health intervention program 1312 (diabetes management). For the patient that is the subject of the UI 1300, item 1314 indicates that the patient does not qualify for the diabetes management program 1312 (as shown by the "negative" indicator). The component expression that is utilized to determine if the patient qualifies for the diabetes management program 1312 is shown at 1315 in a tree-like form. This is just one exemplary way of depicting the component expression 1315 and is not meant to be limiting. The component expression 1315 includes logical operators 1322 and 1324 and components 1316, 1317, and 1318. Components in the component expression 1315 that are satisfied by the patient's data, such as the components 1316 and 1317, may be emphasized in some way such as by bolding the font, displaying the font in a certain color such as green, and in other ways known in the art. Components that are not satisfied by the patient's data, such as the component 1318, may be displayed in such a way as to emphasize that the component 1318 is not satisfied such as by graying out the component 1318, displaying the font in a certain color such as red, and the like.

Each of the components 1316, 1317, and 1318 in the component expression 1315 is actionable. For example, a user can hover over or select a particular component and initiate the display of information related to the component. This holds true whether the component is satisfied (such as the components 1316 and 1317) or is not satisfied such as the component 1318. The information may include a textual narrative of, for example, sub-criteria associated with the component and supporting facts associated with the component. With respect to the component 1318 that is not satisfied by the patient's data, the information presented in the pop-up box 1320 includes which of the component's sub-criteria is met and which of the component's sub-criteria disqualified the patient from the diabetes management program 1312. For example, with respect to the component 1318, the component was not met because the value sub-criteria for BMI (body mass index) was not met. The information in the pop-up box 1320 also includes the clinical value for the patient's BMI (i.e., the supporting fact). As seen in UI 1300, the present invention provides easy explainability to an end-user on why a particular patient failed to qualify for a health intervention program.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. One or more non-transitory computer-storage media having computer-executable instructions embodied thereon that, when executed by a server comprising a plurality of batch processing nodes, facilitate a method of identifying members of a population who qualify for one or more health intervention programs, the method comprising:

receiving, by the server, one or more sets of raw patient population health data, the one or more sets of raw patient population health data received in a plurality of disparate formats from one or more of healthcare facilities;

automatically converting, by the server utilizing a first set of the plurality of batch processing nodes, the one or more sets of raw patient population health data from the plurality of disparate formats to a standard format and automatically grouping the standardized one or more sets of raw patient population health data into one or more high-level domain-specific constructs;

storing, by the server, the one or more high-level domain-specific constructs in a distributed storage system comprising a plurality of distributed storages, wherein each one of the plurality of distributed storages is physically co-located with a particular one of the first set of the plurality of batch processing nodes, wherein the one or more healthcare facilities are provided real-time access to the one or more high-level domain-specific constructs stored in the distributed storage system;

receiving, by the server, a document in human-readable form, the document corresponding to the one or more health intervention programs;

identifying in the document, by the server utilizing the first set of the plurality of batch processing nodes, a set of concepts by identifying a set of nouns representing the set of concepts in the document;

identifying in the document, by the server utilizing the first set of the plurality of batch processing nodes, a set of concept-specific functions by identifying one or more of a set of verbs, a set of conditions for the set of concepts, and a set of characteristics for the set of concepts in the document, wherein the one or more of the set of verbs, the set of conditions for the set of concepts, and the set of characteristics for the set of concepts correspond to the set of concepts and represent the set of concept-specific functions;

using the set of concepts and the set of concept-specific functions identified in the document to generate, by the server utilizing the first set of the plurality of batch processing nodes, computer-readable code that corresponds to the document in human-readable form, the computer-readable code comprising a first set of high-level clinical logic;

storing, by the server utilizing the first set of the plurality of batch processing nodes, the first set of high-level clinical logic in the distributed storage system;

executing, by the server, the first set of high-level clinical logic against the one or more high-level domain-specific constructs to identify one or more members of the population who qualify for the one or more health intervention programs;

providing, by the server, over a computer network to the one or more healthcare facilities a notification of the identification of the one or more members of the population who qualify for the one or more health intervention programs;

Continuously monitoring and receiving, by the server, one or more updates to the one or more sets of raw patient population health data in real-time in the plurality of disparate formats from at least one of the one or more healthcare facilities;

automatically converting, by the server utilizing a second set of the plurality of batch processing nodes, the one or more updates to the one or more sets of raw patient population health data from the plurality of disparate formats to the standard format and automatically grouping the one or more sets of standardized updated patient population health data into one or more updated high-level domain-specific constructs;

storing, by the server, the one or more updated high-level domain-specific constructs in the distributed storage system and providing the one or more healthcare facilities real-time access to the one or more updated high-level domain-specific constructs stored in the distributed storage system;

executing, by the server utilizing the second set of the plurality of batch processing nodes, the first set of high-level clinical logic against the one or more high-level domain-specific constructs and the one or more updated high-level domain-specific constructs to generate an updated identification of the one or more members of the population who qualify for the one or more health intervention programs and storing the updated identification of the one or more members of the population who qualify for the one or more health intervention programs in the outcome data store; and automatically providing, by the server, over the computer network to the one or more healthcare facilities a second notification of the updated identification of the one or more members of the population who qualify for the one or more health intervention programs.

2. The media of claim 1, wherein the one or more sets of patient population health data are received from electronic medical record systems associated with one or more healthcare facilities.

3. The media of claim 2, wherein the one or more sets of patient population health data are received in disparate formats.

4. The media of claim 1, wherein prior to storing the one or more sets of population health data in association with the distributed storage system, the one or more sets of population health data are minimally processed using concept mapping and concept grouping.

5. The media of claim 1, wherein the first set of high-level clinical logic is a declarative language such that high-level concepts are utilized to describe a subset of patient population health data within the one or more sets of patient population health data that is of interest.

6. The media of claim 5, wherein the first set of high-level clinical logic is healthcare-domain specific.

7. The media of claim 5, wherein execution of the first set of high-level clinical logic is independent of the underlying data format associated with the one or more sets of patient population health data.

8. The media of claim 1, wherein the first set of high-level clinical logic is further utilized to render a visual representation of the high-level clinical logic on a user interface.

9. The media of claim 8, wherein the visual representation implicitly defines an audit trail.

10. The media of claim 1, further comprising executing a second set of high-level clinical logic against the one or more sets of patient population health data to stratify the one or more members of the population based on degree of risk.

11. The media of claim 10, further comprising executing a third set of high-level clinical logic against the one or more sets of patient population health data to monitor health data related to the one or more members of the population who qualify for the one or more health intervention programs.

12. A computer-implemented system for processing and updating population health data, the system comprising:
a runtime engine comprising:
a plurality of batch processing nodes operable to:
(1) receive one or more sets of patient population health data, the one or more sets of raw patient population health data received in a plurality of disparate formats over a computer network from a one or more healthcare facilities,
(2) automatically convert the one or more sets of raw patient population health data from the plurality of disparate formats to a standard format and automatically group the standardized one or more sets of raw patient population health data into one or more high-level domain-specific constructs,
(3) store the one or more high-level domain-specific constructs in a distributed storage system comprising a plurality of distributed storages, wherein each one of the plurality of distributed storages is physically co-located with a particular one of the first set of the plurality of batch processing nodes, wherein the one or more healthcare facilities are provided real-time access to the one or more high-level domain-specific constructs stored in the distributed storage system,
(4) receive a document in human-readable form, the document corresponding to the health intervention program,
(5) identify in the document a set of concepts by identifying a set of nouns representing the set of concepts in the document, (6) identify in the document a set of concept-specific functions by identifying one or more of a set of verbs, a set of conditions for the set of concepts, and a set of characteristics for the set of concepts in the document, wherein the one or more of the set of verbs, the set of conditions for the set of concepts, and the set of characteristics for the set of concepts correspond to the set of concepts and represent the set of concept-specific functions;

(7) utilize the set of concepts and the set of concept-specific functions identified in the document to generate computer-readable code that corresponds to the document in human-readable form, the computer-readable code comprising a set of high-level clinical logic;

(8) store the set of high-level clinical logic in the distributed storage system, (9) execute a the set of high-level clinical logic against the one or more high-level domain-specific constructs to identify a first set of members of the population who qualify for one or more health intervention programs, and

(10) provide over the computer network to the one or more healthcare facilities a notification of the identification of the first set of members of the population who qualify for the one or more health intervention programs; and a plurality of incremental processing nodes operable to:

(1) continuously monitor and receive one or more updates to the one or more sets of raw patient population health data in real-time in the plurality of disparate formats over the computer network from at least one of the one or more healthcare facilities, (2) automatically convert the one or more updates to the one or more sets of raw patient population health data from the plurality of disparate formats to the standard format and automatically group the one or more sets of standardized updated patient population health data into one or more updated high-level domain-specific constructs, (3) store the one or more updated high-level domain-specific constructs in the distributed storage system and provide the one or more healthcare facilities real-time access to the one or more updated high-level domain-specific constructs stored in the distributed storage system, (4) execute the high-level clinical logic against the one or more high-level domain-specific constructs and the one or more updated high-level domain-specific constructs to identify a second set of members of the population who qualify for the one or more health intervention programs, and (5) automatically provide to the one or more healthcare facilities over the computer network a second notification of the updated identification of the second set of members of the population who qualify for the one or more health intervention programs.

13. The system of claim 12, wherein the one or more sets of patient population health data and the updates to the one or more sets of patient population health data are received from the one or more healthcare facilities located remote to the plurality of processing nodes and the plurality of incremental processing nodes.

14. The system of claim 12, wherein the distributed storage system is physically located in association with the plurality of batch processing nodes.

15. The system of claim 12, wherein the updates to the one or more sets of patient population health data are received in real time.

16. The system of claim 12, wherein a memory cache is associated with each incremental processing node of the plurality of incremental processing nodes.

17. The system of claim 16, wherein the memory cache stores a subset of the one or more sets of patient population health data pertinent to the execution of the high-level clinical logic.

18. One or more non-transitory computer-storage media having computer-executable instructions embodied thereon that, when executed by a server comprising a plurality of batch processing nodes, facilitate of method of managing population health, the method comprising:

receiving, by the server, one or more sets of patient population health data from one or more electronic medical record systems, the one or more sets of raw patient population health data received in a plurality of disparate formats from one or more healthcare facilities;

automatically converting, by the server utilizing a first set of the plurality of batch processing nodes, the one or more sets of raw patient population health data from the plurality of disparate formats to a standard format and automatically grouping the standardized one or more sets of raw patient population health data into one or more high-level domain-specific constructs;

storing, by the server, the one or more high-level domain-specific constructs in a distributed storage system comprising a plurality of distributed storages, wherein each one of the plurality of distributed storages is physically co-located with a particular one of the first set of the plurality of batch processing nodes, wherein the one or more healthcare facilities are provided real-time access to the one or more high-level domain-specific constructs stored in the distributed storage system;

receiving, by the server, a document in human-readable form, the document corresponding to one or more health intervention programs;

identifying in the document, by the server utilizing the first set of the plurality of batch processing nodes, a set of concepts by identifying a set of nouns representing the set of concepts in the document;

identifying in the document, by the server utilizing the first set of the plurality of batch processing nodes, a set of concept-specific functions by identifying one or more of a set of verbs, a set of conditions for the set of concepts, and a set of characteristics for the set of concepts in the document, wherein the one or more of the set of verbs, the set of conditions for the set of concepts, and the set of characteristics for the set of concepts correspond to the set of concepts and represent the set of concept-specific functions;

using the set of concepts and the set of concept-specific functions identified in the document to generate, by the server utilizing the first set of the plurality of batch processing nodes, computer-readable code that corresponds to the document in human-readable form, the computer-readable code comprising a set of high-level clinical logic;

storing, by the server utilizing the first set of the plurality of batch processing nodes, the set of high-level clinical logic in the distributed storage system;

executing, by the server, the set of high-level clinical logic against the one or more high-level domain-specific constructs to identify one or more members of the population who qualify for the one or more health intervention programs;

providing, by the server, over a computer network to the one or more healthcare facilities a notification of the identification of the one or more members of the population who qualify for the one or more health intervention programs;

Continuously monitoring and receiving by the server, over the computer network, one or more sets of updated patient population health data in real-time in the plurality of disparate formats from the one or more electronic medical record systems;

automatically converting, by the server utilizing a second set of the plurality of batch processing nodes, the one or more sets of updated patient population health data from the plurality of disparate formats to the standard format and automatically grouping the one or more sets of standardized updated patient population health data into one or more updated high-level domain-specific constructs;

storing, by the server, the one or more updated high-level domain-specific constructs in the distributed storage system and providing the one or more healthcare facilities real-time access to the one or more updated high-level domain-specific constructs stored in the distributed storage system;

executing, by the server utilizing the second set of the plurality of batch processing nodes, the set of high-level clinical logic against the one or more high-level domain-specific constructs and the one or more updated high-level domain-specific constructs to generate an updated identification of one or more members of the population at risk who qualify for one or more health intervention programs and storing the updated identification of the one or more members of the population who qualify for the one or more health intervention programs in the outcome data store; and automatically providing, by the server, over the computer network to the one or more healthcare facilities a second notification of the updated identification of the one or more members of the population who qualify for the one or more health intervention programs.

19. The media of claim 18, wherein the one or more electronic medical record systems are associated with one or more healthcare facilities.

20. The media of claim 18, wherein the one or more electronic medical record systems store the one or more sets of patient population health data in disparate formats.

* * * * *